(12) United States Patent
Davies et al.

(10) Patent No.: US 9,345,509 B2
(45) Date of Patent: *May 24, 2016

(54) GUIDE-WIRE DILATION DEVICE FOR FACILITATION OF LESION CROSSING

(71) Applicants: Baylis Medical Company Inc., Mississauga (CA); Bradley H. Strauss, Toronto (CA)

(72) Inventors: Gareth Davies, Toronto (CA); Maria Luk, Toronto (CA); Thomas C. Waram, Dundas (CA); Bradley H. Strauss, Toronto (CA)

(73) Assignees: BAYLIS MEDICAL COMPANY INC., Montreal, Quebec (CA); Bradley H. Strauss, Toronto (CA)

( * ) Notice: Subject to any disclaimer, the term of this patent is extended or adjusted under 35 U.S.C. 154(b) by 228 days.

This patent is subject to a terminal disclaimer.

(21) Appl. No.: 14/135,656

(22) Filed: Dec. 20, 2013

(65) Prior Publication Data

US 2014/0107681 A1    Apr. 17, 2014

Related U.S. Application Data

(63) Continuation-in-part of application No. 12/280,379, filed as application No. PCT/CA2007/000285 on Feb. 22, 2007, now Pat. No. 8,617,192.

(60) Provisional application No. 60/775,327, filed on Feb. 22, 2006, provisional application No. 61/773,878, filed on Mar. 7, 2013.

(51) Int. Cl.
*A61B 17/22* (2006.01)
*A61B 17/3207* (2006.01)
(Continued)

(52) U.S. Cl.
CPC ..... *A61B 17/320725* (2013.01); *A61B 17/3207* (2013.01); *A61M 29/00* (2013.01);
(Continued)

(58) Field of Classification Search
CPC ............... A61B 17/3207; A61B 2017/320056; A61B 2017/320741; A61M 2025/0197; A61M 25/0021; A61M 25/0043; A61M 25/0045; A61M 25/0054; A61M 25/0067; A61M 25/0068; A61M 25/0069; A61M 25/0194; A61M 29/00

See application file for complete search history.

(56) References Cited

U.S. PATENT DOCUMENTS 2,944,552 A * 7/1960 Cannon ............ A61B 17/32053
30/316

(Continued)

FOREIGN PATENT DOCUMENTS

WO    WO99/56801 A2    11/1999
WO    WO0219928 A2    3/2002

OTHER PUBLICATIONS

European Search Report of Application No. 07710640.9 mailed on Aug. 16, 2013.
(Continued)

*Primary Examiner* — Ryan J Severson
(74) *Attorney, Agent, or Firm* — Nir Lifshitz; Glenn Arnold

(57) ABSTRACT

Devices and methods are disclosed for widening a channel in a treatment site, the channel containing a guide-wire. The channel is widened by advancing an elongated dilation device, which is configured to fit tightly over the guide-wire at the distal tip of the dilation device and to provide a distal dilating surface, over the guide-wire and at least partially through the treatment site. The dilation device comprises a tubular metallic shaft, typically a metal inner tube, for providing sufficient stiffness and column strength for the dilator to be advanced at least partially through the channel, and a flexible sleeve providing a tapered distal tip. The distal end of the dilator defines a leading surface that is shaped to force away portions of a lesion surrounding the guide-wire away from the guide-wire as the distal end is advanced over the guide-wire through the lesion, whereby a channel through the lesion is at least partially dilated.

22 Claims, 23 Drawing Sheets

(51) Int. Cl.
*A61M 29/00* (2006.01)
*A61B 17/32* (2006.01)
*A61M 25/00* (2006.01)
*A61M 25/01* (2006.01)

(52) U.S. Cl.
CPC ............. *A61B2017/320044* (2013.01); *A61B 2017/320056* (2013.01); *A61M 25/0021* (2013.01); *A61M 25/0045* (2013.01); *A61M 25/0051* (2013.01); *A61M 2025/0047* (2013.01); *A61M 2025/0183* (2013.01)

(56) References Cited

U.S. PATENT DOCUMENTS

| | | | | |
|---|---|---|---|---|
| 3,094,124 A * | 6/1963 | Birtwell | A61M 25/00 | 604/523 |
| 3,683,891 A * | 8/1972 | Eskridge | A61B 10/04 | 30/113.1 |
| 3,749,085 A * | 7/1973 | Willson | A61B 10/04 | 600/570 |
| 4,290,427 A * | 9/1981 | Chin | A61B 17/320016 | 606/159 |
| 4,315,511 A * | 2/1982 | Chin | A61B 17/32075 | 15/104.16 |
| 4,559,927 A * | 12/1985 | Chin | A61B 17/22 | 128/898 |
| 4,574,781 A * | 3/1986 | Chin | A61B 17/22 | 15/104.16 |
| 4,597,389 A * | 7/1986 | Ibrahim | A61B 17/22032 | 604/908 |
| 4,653,496 A * | 3/1987 | Bundy | A61B 17/3207 | 600/564 |
| 4,732,154 A * | 3/1988 | Shiber | A61B 17/22012 | 606/108 |
| 4,776,844 A | 10/1988 | Ueda | | |
| 4,862,891 A * | 9/1989 | Smith | A61B 17/3417 | 604/104 |
| 4,883,458 A * | 11/1989 | Shiber | A61B 8/12 | 604/22 |
| 4,886,490 A * | 12/1989 | Shiber | A61B 8/12 | 604/22 |
| 4,898,574 A | 2/1990 | Uchiyama et al. | | |
| 4,898,575 A * | 2/1990 | Fischell | A61B 17/3207 | 604/22 |
| 5,041,082 A * | 8/1991 | Shiber | A61B 17/22012 | 604/22 |
| 5,041,089 A * | 8/1991 | Mueller | A61M 25/104 | 604/103 |
| 5,047,040 A * | 9/1991 | Simpson | A61B 17/3207 | 604/22 |
| 5,075,014 A | 12/1991 | Sullivan | | |
| 5,078,723 A * | 1/1992 | Dance | A61B 17/3207 | 604/22 |
| 5,127,902 A * | 7/1992 | Fischell | A61B 17/32075 | 604/22 |
| 5,127,917 A * | 7/1992 | Niederhauser | A61B 17/22012 | 600/434 |
| 5,205,830 A * | 4/1993 | Dassa | A61M 25/0068 | 604/164.1 |
| 5,306,244 A * | 4/1994 | Shiber | A61B 8/12 | 600/585 |
| 5,327,885 A * | 7/1994 | Griffith | A61B 8/12 | 600/470 |
| 5,496,344 A * | 3/1996 | Kanesaka | A61M 29/02 | 604/264 |
| 5,573,520 A * | 11/1996 | Schwartz | A61M 25/0013 | 604/264 |
| 5,665,098 A * | 9/1997 | Kelly | A61B 17/32075 | 604/22 |
| 5,879,808 A | 3/1999 | Wary et al. | | |
| 6,036,708 A * | 3/2000 | Sciver | A61B 17/320783 | 606/159 |
| 6,083,232 A * | 7/2000 | Cox | A61B 17/22012 | 601/2 |
| 6,143,009 A * | 11/2000 | Shiber | A61B 17/320758 | 606/159 |
| 6,482,215 B1 * | 11/2002 | Shiber | A61B 17/320758 | 606/159 |
| 6,514,217 B1 | 2/2003 | Selmon et al. | | |
| 6,663,617 B1 * | 12/2003 | Vito | A61F 2/06 | 600/36 |
| 6,824,560 B2 * | 11/2004 | Pelton | A61F 2/91 | 600/36 |
| 7,578,042 B2 * | 8/2009 | Magnuson | A61M 25/001 | 29/521 |
| 7,704,245 B2 * | 4/2010 | Dittman | A61M 25/0012 | 604/523 |
| 7,909,779 B2 * | 3/2011 | Shimogami | A61M 25/0012 | 600/585 |
| 8,011,079 B2 * | 9/2011 | Magnuson | A61M 25/001 | 29/521 |
| 8,574,192 B2 * | 11/2013 | Haarala | A61B 17/3415 | 604/104 |
| 8,617,192 B2 * | 12/2013 | Strauss | A61B 17/320708 | 606/159 |
| 2002/0087076 A1 * | 7/2002 | Meguro | A61M 25/0021 | 600/433 |
| 2002/0099397 A1 | 7/2002 | Sparks | | |
| 2002/0133128 A1 * | 9/2002 | Heller | A61B 17/3421 | 604/270 |
| 2002/0156459 A1 * | 10/2002 | Ye | A61L 29/085 | 604/527 |
| 2003/0216761 A1 * | 11/2003 | Shiber | A61B 8/12 | 606/159 |
| 2004/0220549 A1 * | 11/2004 | Dittman | A61M 25/0012 | 604/526 |
| 2005/0027309 A1 * | 2/2005 | Shiber | A61B 17/3207 | 606/159 |
| 2005/0222585 A1 * | 10/2005 | Miyata | A61M 25/0021 | 606/113 |
| 2005/0228364 A1 * | 10/2005 | Braga | A61B 17/3415 | 606/1 |
| 2005/0273074 A1 * | 12/2005 | Lewis | A61M 25/0068 | 604/508 |
| 2005/0288628 A1 | 12/2005 | Jordan et al. | | |
| 2006/0074442 A1 * | 4/2006 | Noriega | A61B 17/32002 | 606/159 |
| 2006/0116661 A1 * | 6/2006 | Tanghoej | A61M 25/0017 | 604/540 |
| 2006/0178653 A1 * | 8/2006 | Shimogami | A61M 25/0012 | 604/526 |
| 2006/0217664 A1 * | 9/2006 | Hattler | A61M 25/0668 | 604/164.1 |
| 2007/0005084 A1 * | 1/2007 | Clague | A61B 17/00008 | 606/159 |
| 2007/0244440 A1 * | 10/2007 | Pal | A61M 25/0074 | 604/164.13 |
| 2007/0287957 A1 * | 12/2007 | Magnuson | A61M 25/0012 | 604/103.1 |
| 2008/0154293 A1 * | 6/2008 | Taylor | A61B 17/32053 | 606/170 |
| 2008/0214992 A1 * | 9/2008 | Haarala | A61B 17/3415 | 604/44 |
| 2009/0030400 A1 * | 1/2009 | Bose | A61M 25/0023 | 604/510 |
| 2009/0030426 A1 * | 1/2009 | Zinn | A61B 17/3415 | 606/108 |
| 2009/0054872 A1 * | 2/2009 | Magnuson | A61M 25/001 | 604/523 |
| 2009/0054875 A1 * | 2/2009 | Strauss | A61B 17/320708 | 604/528 |
| 2009/0138031 A1 * | 5/2009 | Tsukernik | A61B 17/320758 | 606/159 |
| 2009/0247987 A1 * | 10/2009 | Chevalier, Jr. | A61M 25/005 | 604/525 |
| 2010/0030251 A1 * | 2/2010 | Sandhu | A61B 17/3207 | 606/194 |
| 2010/0031491 A1 * | 2/2010 | Magnuson | A61M 25/001 | 29/521 |
| 2011/0245775 A1 * | 10/2011 | Tekulve | A61M 25/0045 | 604/171 |
| 2012/0083794 A1 * | 4/2012 | Martin | A61B 17/3415 | 606/108 |

(56) References Cited

U.S. PATENT DOCUMENTS

2012/0101480 A1* 4/2012 Ingle ............... A61M 25/0009
 604/526
2012/0209176 A1* 8/2012 Anderson .......... A61B 17/3207
 604/103.02
2014/0107681 A1* 4/2014 Davies ............... A61B 17/3207
 606/159

OTHER PUBLICATIONS

Total across brochure. Medtronic, Inc. Published in 2013.

* cited by examiner

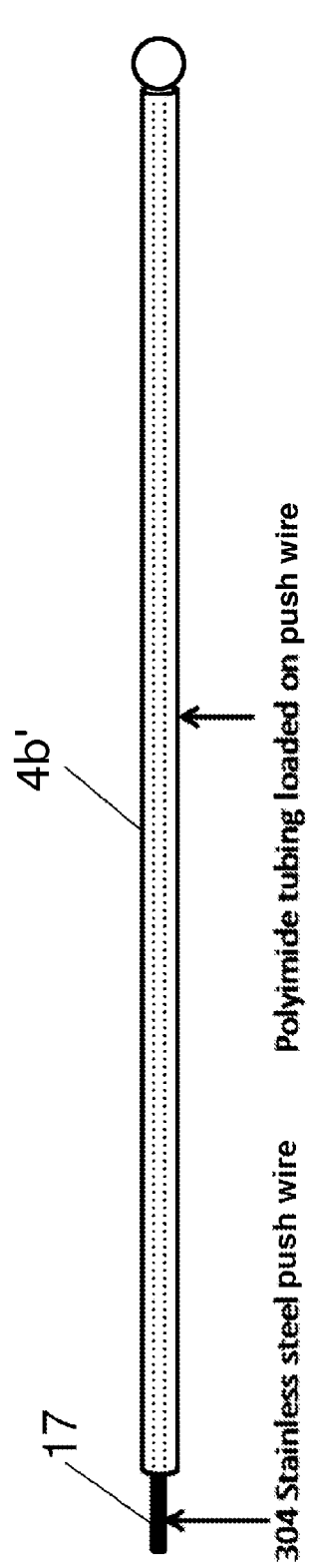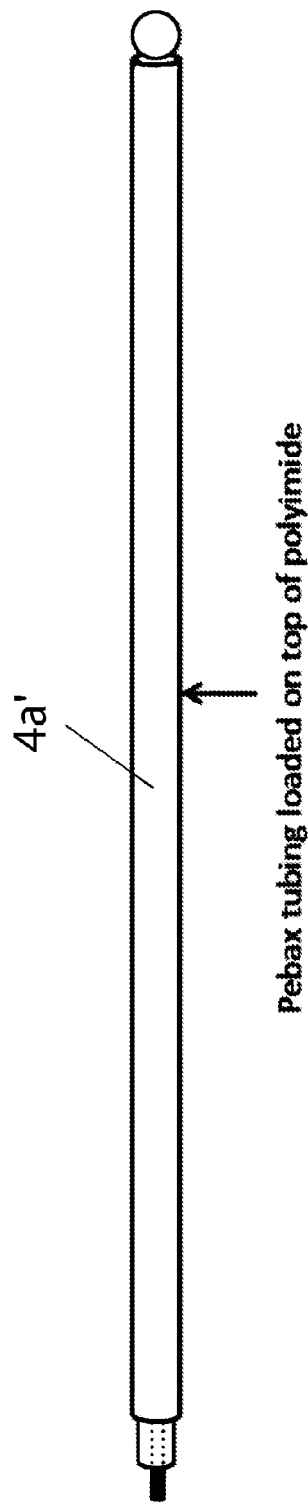
Fig. 15a
Fig. 15b

PET shrunk over overlap

Pebax loaded over top

GUIDE-WIRE DILATION DEVICE FOR FACILITATION OF LESION CROSSING

CROSS-REFERENCE TO RELATED APPLICATIONS

This application is a Continuation-in-Part of co-pending U.S. application Ser. No. 12/280,379, which is the national phase application (national phase entry date Nov. 11, 2008) of international application No. PCT/CA2007/000285, filed Feb. 22, 2007, published in English Aug. 30, 2007, which claims priority to U.S. provisional application No. 60/775,327 filed Feb. 22, 2006, all of which are incorporated herein by reference. This application also claims priority to U.S. provisional application No. 61/773,878, filed Mar. 7, 2013, incorporated herein by reference.

TECHNICAL FIELD

This invention relates to the field of vessel repair, and more particularly relates to advancing a dilation device through a narrowed or closed vessel of a treatment site and the expansion of a channel through the vessel.

BACKGROUND

U.S. Pat. No. 4,898,574 (Fischell) relates to an atherectomy (tunneling catheter) device used to remove plaque and enlarge a channel through an occlusion previously crossed by a guide-wire to thereby increase blood flow. The Fischell device primarily functions as a coring device that removes tissue and includes a sharp cutting edge to cut a cylindrical bore of tissue from the occlusion and uses suction to hold it within the device. Fischell's tunneling catheter is typically comprised of a stainless steel cylinder, wherein the stainless steel cylinder tapers distally to define the cutting edge. As described, Fischell's device has an inner lumen much greater than the associated guide-wire to allow for sufficient suction and to provide space for storage of occlusive material. All of the disclosed embodiments of Fischell are for over-the-wire type devices.

SUMMARY OF THE DISCLOSURE

The problem of widening a channel containing a guide-wire in a treatment site is solved by advancing an elongated dilation device over the guide-wire and at least partially through the treatment site. The dilation device is sufficiently flexible to be advanced to the treatment site, and its distal tip is tapered and configured to fit well over the guide-wire, thereby providing a dilating leading surface. The dilation device has a tubular metal shaft, typically a metal inner tube, for providing sufficient stiffness and column strength to advance the device at least partially through the channel. A flexible sleeve of the device provides a tapered distal tip.

In one broad aspect, embodiments of the present invention comprise a dilation device installable on a guide-wire inserted through a vessel having a lesion therein. The dilation device comprises a metallic shaft defining a lumen and a polymer sleeve substantially covering the metallic shaft. A distal end of the dilation device is sized for fitting receipt of the guide-wire therethrough, with the distal end defining a leading surface that is shaped to force away portions of the lesion surrounding the guide-wire away from the guide-wire as the distal end is advanced over the guide-wire through the lesion, whereby a channel through the lesion is at least partially dilated. Typically, the leading surface of the dilator is provided by the polymer sleeve.

Another broad aspect is for a kit comprising the above described dilation device and a guide-wire, wherein a diameter of the guide-wire ranges from about 93% to about 97% of the inner diameter of the distal tip (i.e. the distal end) of the dilation device, and from about 80% to about 93% of the inner diameter of the metallic shaft i.e. the diameter of the main lumen. Some examples of kits include: a dilator wherein the distal tip inner diameter is about 0.015 inches (about 0.38 mm) and the metallic shaft inner diameter ranges from about 0.018 inches (about 0.46 mm) to about 0.020 inches (about 0.51 mm), along with a guide-wire having a diameter of about 0.014 inches (about 0.36 mm); a dilator wherein the distal tip inner diameter is about 0.019 inches (about 0.48 mm) and the metallic shaft inner diameter ranges from about 0.020 inches (about 0.51 mm) to about 0.022 inches (about 0.56 mm), along with a guide-wire having a diameter of about 0.018 inches (about 0.46 mm); and a dilator wherein the distal tip inner diameter is about 0.036 inches (about 0.91 mm) and the metallic shaft inner diameter ranges from about 0.038 inches (about 0.97 mm) to about 0.040 inches (1.0 mm), along with a guide-wire having a diameter of about 0.035 inches (about 0.89 mm).

BRIEF DESCRIPTION OF THE DRAWINGS

In order that the invention may be readily understood, embodiments of the invention are illustrated by way of examples in the accompanying drawings, in which:

FIGS. 15a and 15b show the stages of constructing an embodiment of a proximal shaft of a monorail embodiment of the device;

DETAILED DESCRIPTION

Figure 1:
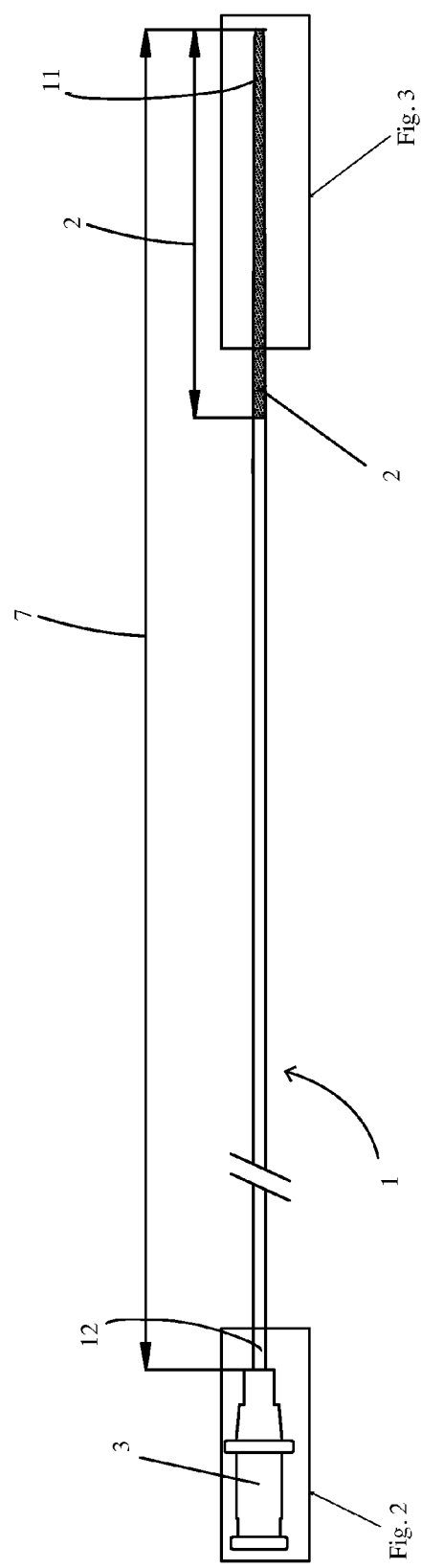
FIG. 1 illustrates a full assembly of an over-the-wire (OTW) embodiment of the device.

Percutaneous coronary interventions are an important form of coronary artery revascularization therapy. In most cases, crossing the lesion with guide-wires and angioplasty and stent catheters is quite straightforward. However, in a particular subgroup of coronary lesions, e.g., chronic total occlusions or heavily calcified, non-compliant stenosis, crossings with balloon angioplasty catheters and stent catheters remain a challenge despite successful crossing with a guide-wire. Thus, there is a need to be able to treat lesions to facilitate balloon angioplasty or stent catheter passage across an arterial occlusion or stenosis after the guide-wire has successfully crossed.

In accordance with embodiments of the present invention, devices and methods are disclosed for widening a channel containing a guide-wire in a treatment site containing an occlusion, a narrowing, or some obstruction. In some cases the guide-wire has been previously inserted to create a channel (e.g. inserted through an occlusion) while in other cases the guide-wire has been previously inserted through an already existing channel (e.g. inserted through a stenosis). To treat a lesion in a vessel, an elongated dilation device including a tubular metallic shaft covered by a polymer sleeve, and a tapered distal tip (typically provided by a polymer tip) that fits closely on the guide-wire at the distal tip of the device, is advanced over the guide-wire and through the treatment site to thereby function as a wedge to widen the channel. Embodiments of the device are disclosed that function as a dilation device and that are not for coring tissue i.e. the embodiments are not intended or structured for cutting and removal of tissue. The inventors have conceived of a dilation device that satisfies two apparently contradictory requirements, flexibility and pushabilty, while allowing for channel dilation. The dilation device, including the tubular metallic shaft, has sufficient flexibility to allow for navigation of the device around bends and other torturous anatomical structures during insertion and removal, while providing sufficient column strength for the dilation device to be advanced at least partially through the channel.

Typical embodiments of the dilator include the tubular metallic shaft comprising a metal tube having constant inner and outer diameters, and having a helical-shaped cut along a distal portion length, whereby the metallic shaft can provide for force transmission from its proximal end to its distal while having a low profile and maintaining flexibility to enable it to be advanced through tortuous vasculature. Furthermore, some embodiments of the disclosed dilator include a polymer sleeve extending distally beyond the metallic shaft to define a polymer tip which has a smaller inner diameter than the metallic shaft. In such embodiments, the inner diameter of the polymer distal tip is sized to closely fit a corresponding guide-wire to allow the dilator to effectively wedgingly displace lesion material without coring and with minimal tissue removal. The relatively larger inner diameter of the metallic shaft enables the dilator to travel over the guide-wire with less friction than if the metallic shaft inner diameter were as small as the polymer tip's inner diameter, thereby reducing the amount of force needed to be applied to the proximal end of the dilator for advancement.

With specific reference now to the drawings in detail, it is stressed that the particulars shown are by way of example and for purposes of illustrative discussion of certain embodiments of the present invention only. It is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

General Device Features

Embodiments of the dilation device include OTW (over-the-wire) and monorail embodiments. For both OTW and monorail embodiments, the distal end of the dilation device is shaped to fit closely over an installed guide-wire and force material away from the guide-wire as the device is advanced over the wire and through the lesion. The device deflects material into the space (typically filled with lesion material) between the device and the vessel and thereby compresses the occlusive tissue against the vessel wall as the device traverses the obstruction. The dilation device can additionally function as a support catheter to support the guide-wire. To assist the surgeon in manipulating the dilation device, it may include at least one radio-opaque marker for visualization. The dilation device may or may not be accompanied, packaged or sold with the guide-wire with which it is to be used. Subsequent to widening a vessel containing a lesion (an occlusion or stenosis), it may become possible to cross the treatment site with a balloon catheter for angioplasty, or to install a stent.

With reference to FIGS. 1 to 6, in typical embodiments of the dilation device, the distal end comprises a metallic shaft 6, which is a metal inner tube, and polymer sleeve 4 comprised of one or more layers of polymer. The inner tube typically has constant inner and outer diameters, which may efficiently provide (i.e. using a minimal amount of metal) sufficient column strength for advancing through resisting material. Some examples of the device include the inner tube being a metal selected from the group consisting of a nickel-titanium (nitinol) alloy, stainless steel, an alloy of cobalt, chromium, nickel and molybdenum (Elgiloy), an alloy of titanium, and combinations thereof. To increase flexibility, a cut (or cuts) can be made into the outer diameter of a portion of the inner tube, with the cut possibly going through the inner tube sidewall i.e. substantially through to the inner surface. In some embodiments the cut (or cuts) made at the distal end portion of the inner tube can be C-shaped cuts, dove-tail cuts or helical-shaped cuts. Some alternative embodiments comprise a braided metallic shaft 6.

Figure 5:
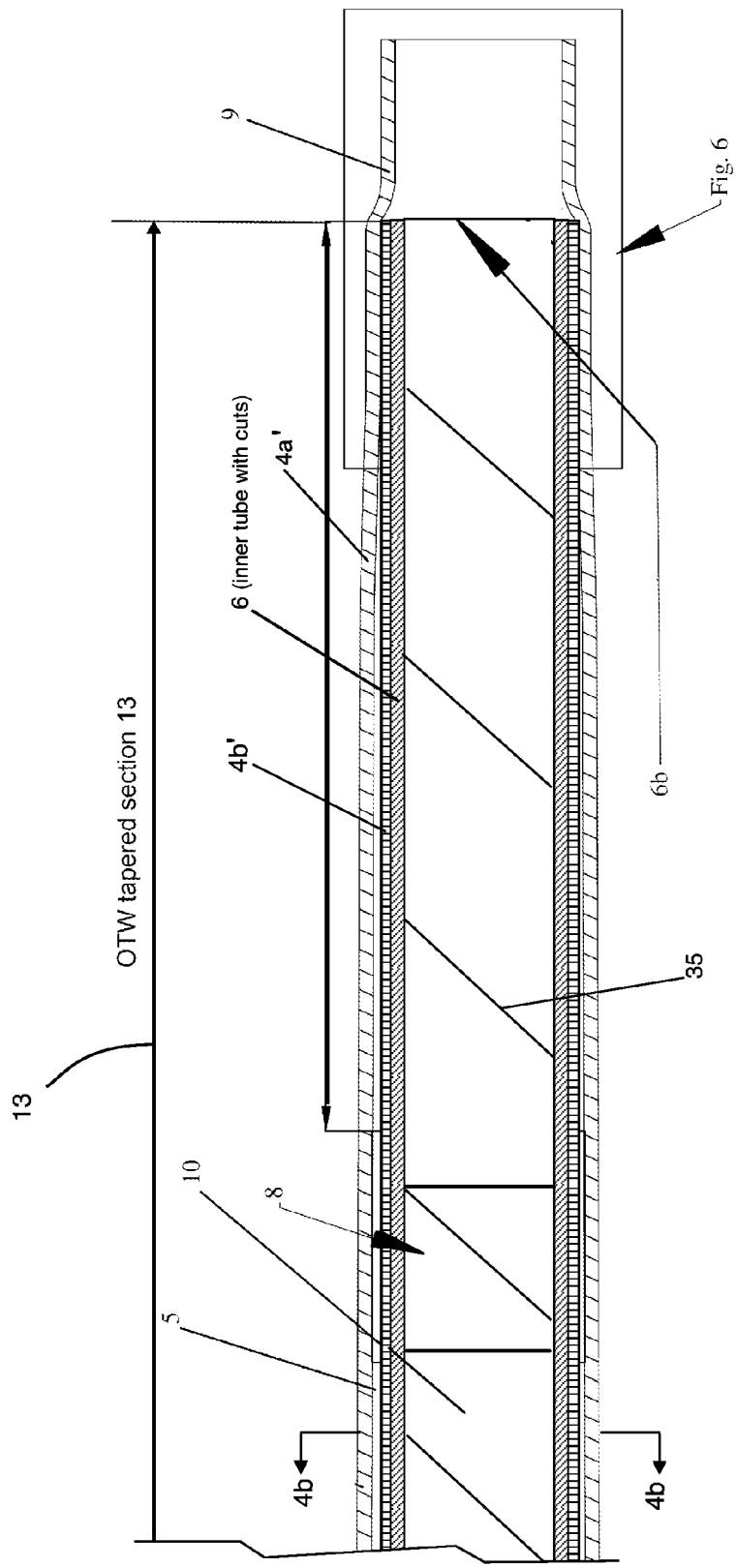
FIG. 5 is an enlarged view of the distal portion of the dilator of FIG. 3.

In typical embodiments of the invention, the polymer sleeve 4 defines the outer diameter of the device, i.e. polymer sleeve 4 forms the outer surface of the device, which decreases distally to form an outer leading surface that slopes proximally outwardly from the distal tip, and the polymer sleeve 4 extends distally beyond metallic shaft 6 to define a polymer distal tip 9 (e.g. FIG. 5). The polymer distal tip typically has a tapering portion (polymer distal tip taper 42) in which the outer diameter of the polymer extension decreases distally to provide a substantially smooth transition from the guide-wire surface to the outer surface of the dilation device. The taper of the polymer extension allows the dilation device to force away portions of the occlusion or stenosis surrounding the inserted guide-wire away from the guide-wire as the device distal end is advanced through the occlusion or stenosis. The inner diameter of the polymer extension is equal to (or slightly larger than) the outer diameter of the corresponding, close fitting guide-wire.

The term "polymer sleeve" used in the description is not intended to be limited to a single layer of flexible polymer or other flexible material. Polymer sleeve 4 can be comprised of one or more layers (or sub-layers) of material and can include polymers including but not limited to nylon, Pebax® (polyether block amide) and/or PTFE (polytetrafluoroethylene) and can include other suitable flexible materials. Typically, the polymer sleeve is heated during installation for a tight fit.

While the sloped leading surface 54 as shown (e.g. FIG. 20), is shaped primarily for pushing material away from the inserted guide-wire instead of shaving or cutting away the material, minor amounts of shaving and/or cutting away can occur. A skilled practitioner can minimize shaving and cutting by, for example, selecting a guide-wire and a dilation device having corresponding diameters.

The sloped surface can taper at different rates, for example, tapering gradually over a longer distance for greater mechanical advantage. A relatively longer taper can help reduce friction, resulting in there being less force required for insertion and easier dilation. To further reduce friction between the outer surface of the device and surrounding tissue, the outer surface of the polymer sleeve of the device may be coated by a hydrophilic coating (a water based polymer). In addition, or alternatively, the leading surface of the dilation device can be rounded to remove sharp edges to thereby help avoid/reduce traumatic damage to the guide-wire and/or vessel inner surfaces.

Some examples of the dilation device also include means for reducing friction between the inner surface of the device (i.e. the surface defining the lumen) and the guide-wire. In some embodiments, the inner surface friction reducing means comprises providing to the inner surface a suitable surface treatment and/or lining the inner surface with a polymer or other material so as to decrease friction with the guide-wire. An example of a suitable surface treatment is electro-polishing. An example of a suitable coating is Parylene C described in U.S. Pat. No. 5,075,014, which issued to Pile on Dec. 24, 1991, and U.S. Pat. No. 5,879,808, which issued to Wary et al. on Mar. 9, 1999. The parylene polymer can be applied by a vapor deposition method, as described in U.S. Pat. No. 5,879,808. In some embodiments, the inner surface defining lumen 10 is lined with PTFE, while in some other embodiments the inner surface is lined with a PTFE/PI (polytetrafluoroethylene/polyimide) blend.

Figure 19:
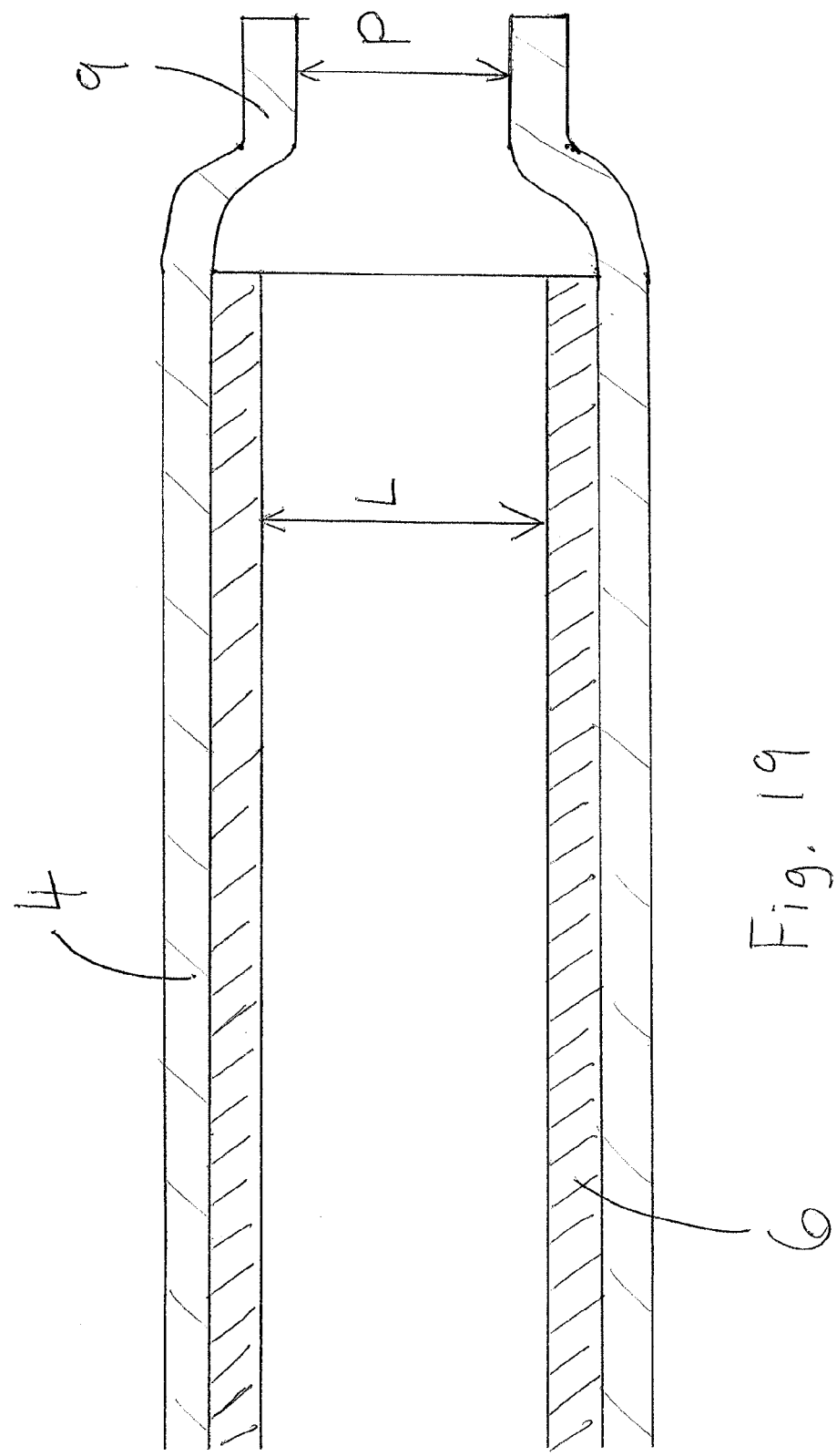
FIG. 19 is a side cutaway view of a distal portion of an embodiment of the device with a narrow distal extension of the polymer sleeve.

FIGS. 19 to 22 illustrate embodiments of the distal portion of the dilation device that may be included in either OTW or monorail embodiments. The embodiment of the device of FIG. 19 illustrates the polymer distal tip 9 of polymer sleeve 4 forming a polymer tip with a distal tip inner diameter P that is smaller than the device's main lumen diameter, (i.e. metallic shaft inner diameter) L defined by metallic shaft 6. While different dimensions for the devices are possible, both OTW and monorail type devices can have embodiments in which: the distal tip inner diameter is about 0.015" (about 0.38 mm) and the metallic shaft inner diameter is between about 0.0175" (0.44 mm) and about 0.020" (about 0.51 mm) ±0.001" (0.025 mm) for use with a guide-wire of about 0.014" (about 0.36 mm) diameter; the distal tip inner diameter is about 0.019" (about 0.48 mm) and the metallic shaft inner diameter is between about 0.020" (about 0.51 mm) and about 0.022" (about 0.56 mm) ±0.001" (about 0.025 mm) for use with a guide-wire of about 0.018" (about 0.46 mm) diameter; or the distal tip inner diameter is about 0.036" (about 0.91 mm) and the metallic shaft inner diameter is between about 0.0375" (about 0.95 mm) and about 0.040" (about 1.0 mm) ±0.001" (about 0.025 mm) for use with a guide-wire of about 0.035" (about 0.89 mm) diameter. Other dimensions and configurations of the device are possible. For example, an alternative embodiment is a dilation device having a polymer tip inner diameter (polymer tip ID) and a main lumen diameter that are substantially equal (e.g. FIG. 21). A practitioner can use embodiments having the above dimensions, along with the corresponding guide-wire, so that the guide-wire is fittingly received to avoid coring of tissue as the device is advanced through an obstructed vessel.

For the embodiments of the previous paragraph, the guide-wire diameters and lumen diameters can be expressed relative to each other as percentages. For example, for the above embodiments, a corresponding guide-wire diameter ranges from about 93% to about 97% of the polymer tip ID (range calculations based on 0.014" guide-wire used with a 0.015" polymer tip ID and a 0.035" guide-wire used with a 0.036" polymer tip ID) and is greater than 78%, for example, about 80% to about 93%, of the main lumen diameter (range based on 0.014" guide-wire used with a 0.0175" main lumen and a 0.035" guide-wire used with a 0.0375" main lumen).

The above described dilators could be used in a system for treating a vessel having a lesion. One embodiment of such a system comprises: an electrical power generator; a radiofrequency guide-wire; and one of the above described dilators wherein a distal end of the dilation device is sized for fitting receipt of the radiofrequency guide-wire therethrough. One example of a suitable radiofrequency guide-wire is the PowerWire™ RF Guidewire, manufactured by Baylis Medical, Montreal, QC, Canada, and described in U.S. application Ser. No. 12/926,292, filed Nov. 8, 2010, incorporated herein by reference.

Figure 20:
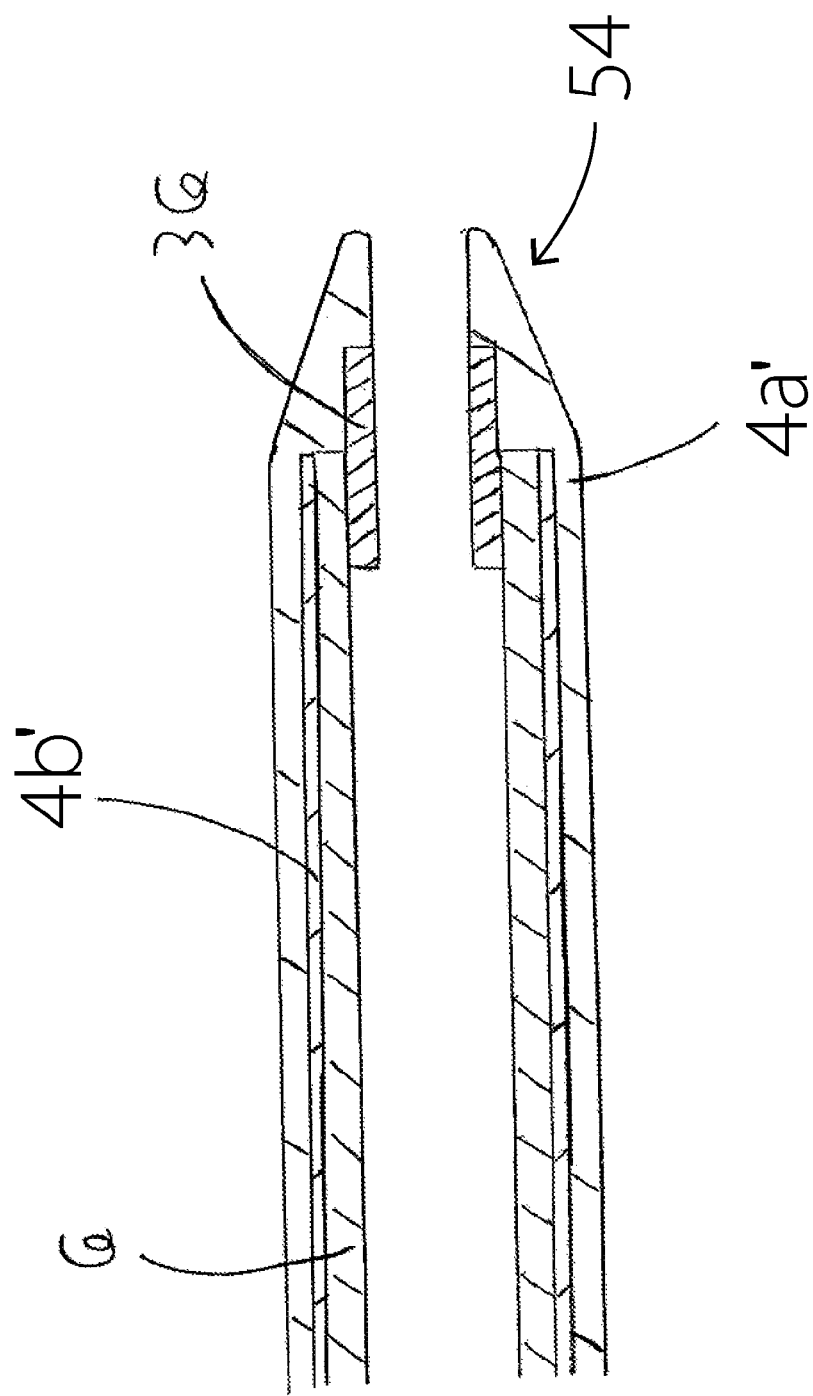
FIG. 20 is a side cutaway view of the end of an embodiment's distal portion with a distal marker.

FIG. 20 is a side cutaway view of an embodiment wherein the distal end includes a tubular-shaped distal end marker 36 at a distal end region of the dilation device, which marker is typically radiopaque. This embodiment also includes an inner polymer layer 4b' (typically PET (polyethylene terephthalate) heat shrink) and an outer polymer layer 4a'. Outer polymer layer 4a' is typically HDPE (high-density polyethylene), but in some alternative embodiments is Pebax®. Distal end marker 36 defines a marker inner diameter substantially equivalent to a distal tip inner diameter defined by the polymer distal tip. While the FIG. 20 embodiment includes distal end marker 36 extending distally from inside of metallic shaft 6 to beyond the distal end of the shaft, alternative embodiments are also possible, such as the distal end of the marker lining up flush with the distal end of metallic shaft 6 (i.e. distal end marker 36 being contained within the lumen defined by metallic shaft 6).

The FIG. 20 embodiment includes a metallic shaft 6 having constant inner and outer diameters substantially along its length, whereby the metallic shaft provides pushability (i.e. the ability of the device to be advanced without buckling) with minimum thickness of metal, thereby keeping the overall device profile (i.e. the outer diameter profile) to a minimum. The constant thickness of metallic shaft 6 also provides for efficient force transmission from the proximal end of the dilation device to the distal end of the device. FIG. 20 also includes an example of the distal end taper being provided by the polymer sleeve.

Figure 21:
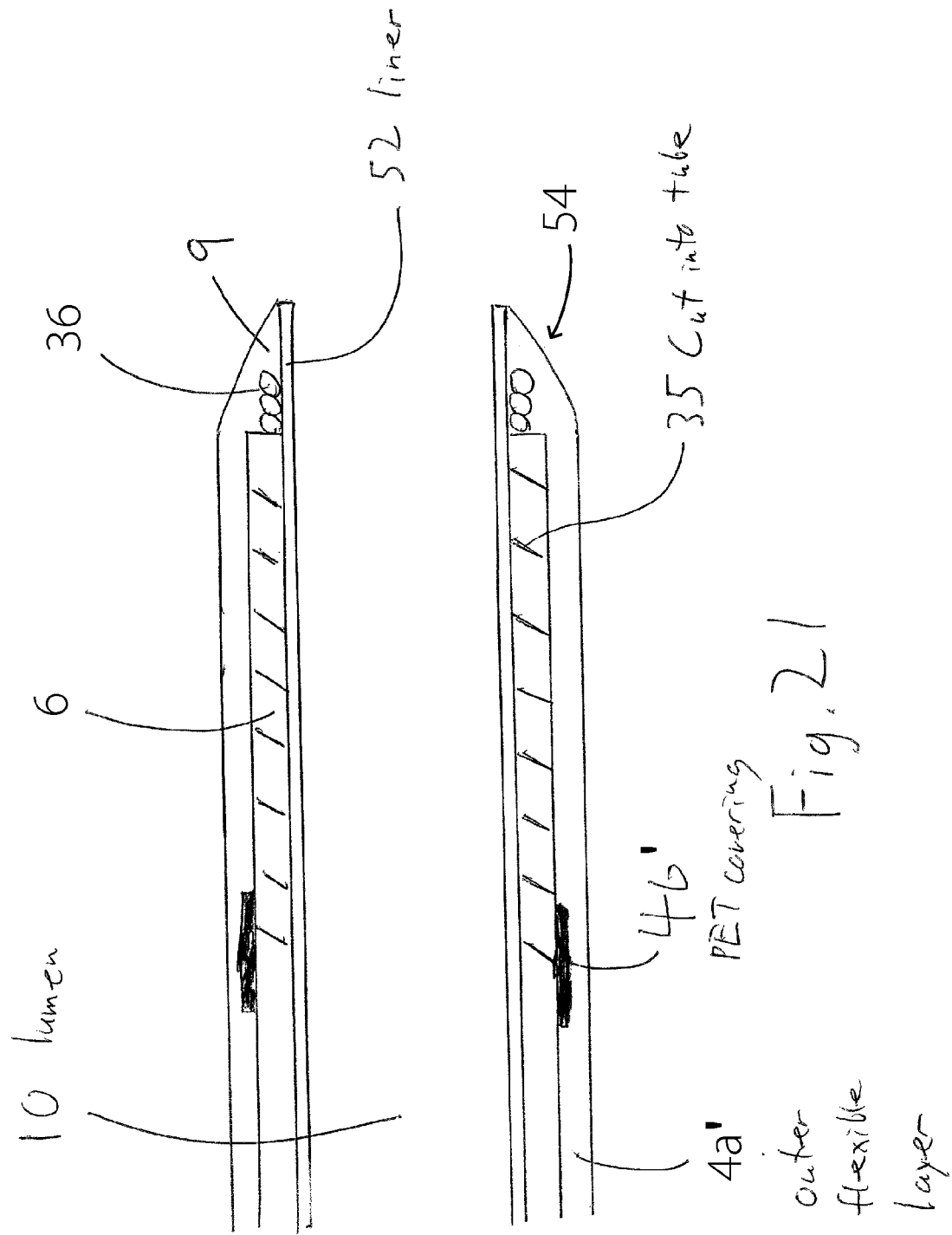
FIG. 21 is a side cutaway view of a distal portion of an alternative embodiment with a coil marker.

FIG. 21 is a side cutaway view of a distal portion of an alternative embodiment. The embodiment of FIG. 21 includes: inner liner 52 defining a lumen 10; metallic shaft 6 (a metal inner tube) having helical cut 35 in a distal portion of the tube; inner polymer layer 4b' (a PET) over the part of metallic shaft 6 that transitions from cut to uncut; an outer polymer layer 4a' which includes a polymer distal tip 9; and a distal end marker 36, which is a radiopaque coil, at a distal end region of the dilation device. In some such embodiments: inner liner 52 is a PTFE/polyimide blend; metallic shaft 6 is a stainless steel hypotube; outer polymer layer 4a' is a Pebax® outer jacket; and distal end marker 36 comprises platinum. Helical cut 35 is typically cut into the outer surface of a metal tube such as a hypotube. In alternative embodiments, inner liner 52 is a PTFE blend. Distal end marker 36 may be comprised of other radiopaque materials, for example, gold, palladium-based alloys, tungsten, or tantalum. Distal end marker 36 defines a marker inner diameter substantially equivalent to a metallic shaft inner diameter defined by the metallic shaft. In the example of FIG. 21, the PET covering (inner polymer layer 4b') is about 20 mm (approximately 0.79 inches) in length while in alternative embodiments it may extend to the distal end of metallic shaft 6 to reinforce the entire portion of the hypotube having helical cut 35. In one particular embodiment: inner liner 52 has an inner diameter of about 0.021 inches (about 0.53 mm) and an outer diameter of about 0.023 inches (about 0.58 mm); metallic shaft 6 has an outer diameter of about 0.0275 inches (about 0.70 mm); and outer polymer layer 4a' has an outer diameter of about 0.030 inches (about 0.76 mm). Although inner liner 52 is shown as having a constant inner and outer diameter, in some embodiments, inner liner 52 tapers inwardly about polymer distal tip 9 such that the inner diameter of the device is reduced, thereby providing a closer fit with a corresponding guide-wire.

Figure 22:
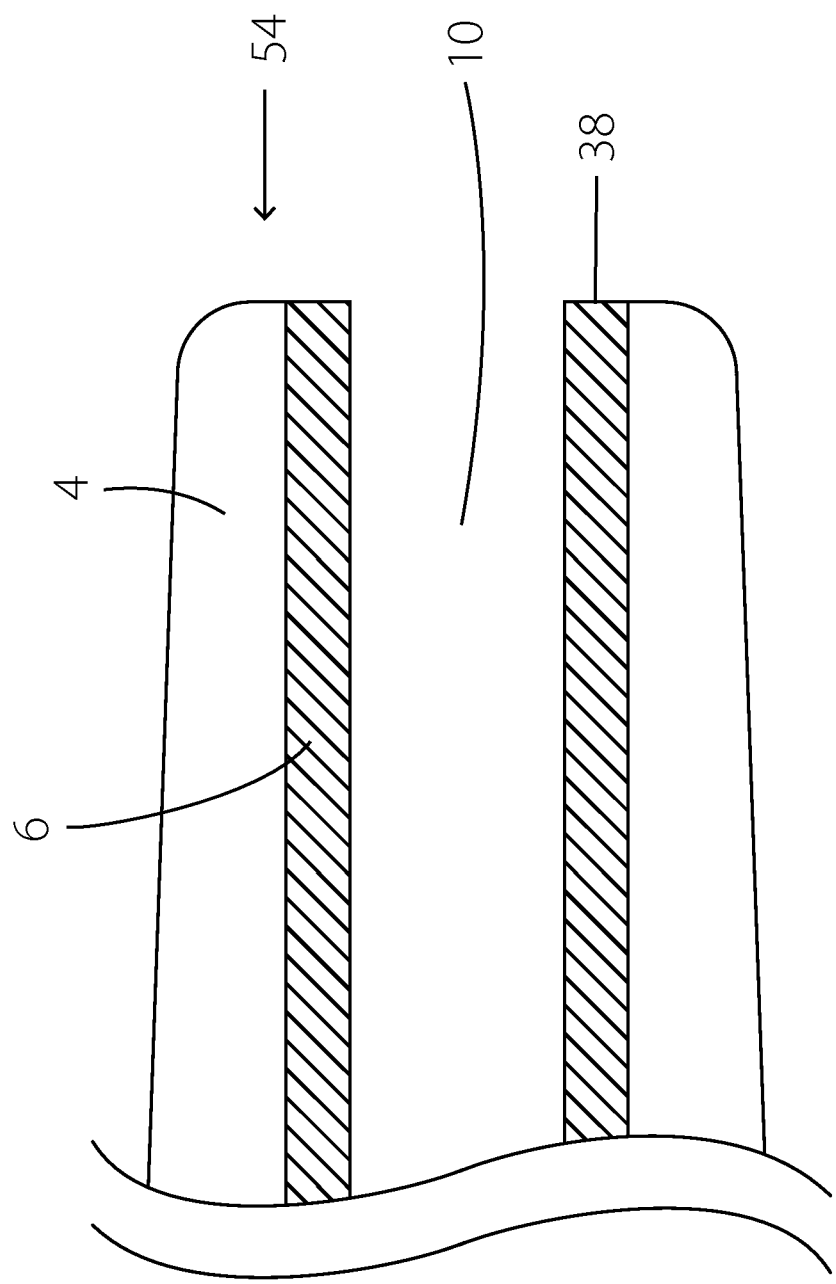
FIG. 22 is side cutaway view of a distal portion of an alternative embodiment that lacks a polymer distal tip.

FIG. 22 is an embodiment of the dilator which does not have a polymer distal tip which extends distally of metallic shaft 6, such that in FIG. 22 the end surface 38 or face of metallic shaft 6 is left exposed. Polymer sleeve 4 is tapered to provide for wedging displacement of lesion material when dilator 1 is advanced, and leading surface 54 is comprised of a distal portion of polymer sleeve 4 and the end surface 38 of metallic shaft 6.

OTW

Figure 2:
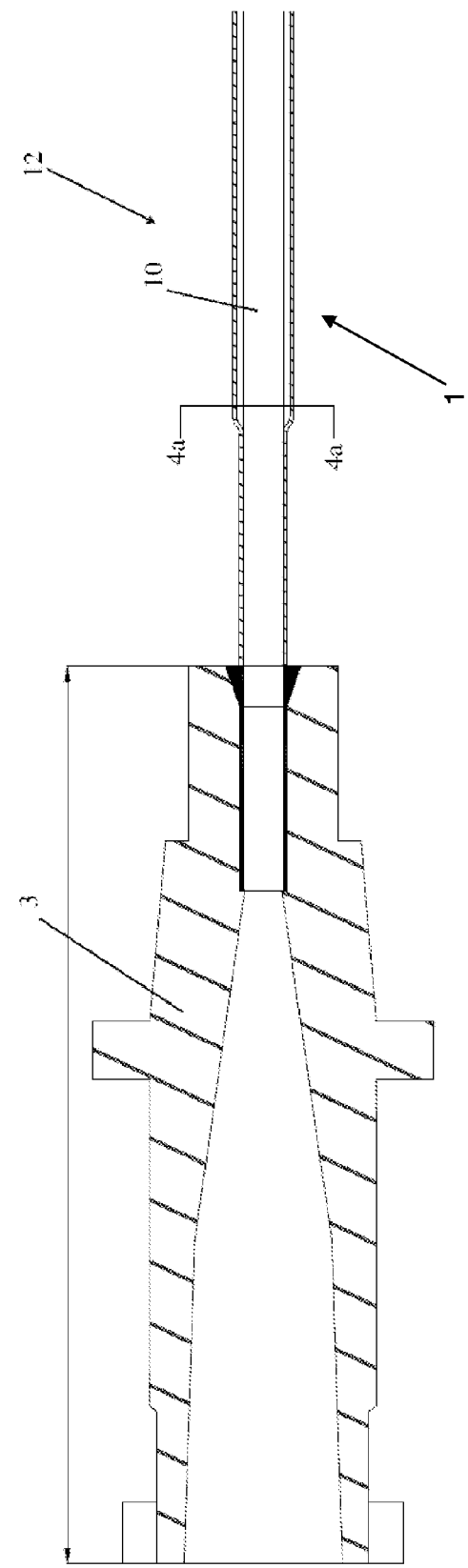
FIG. 2 is a side cutaway view of a proximal portion of the device of the embodiment of FIG. 1.
Figure 3:
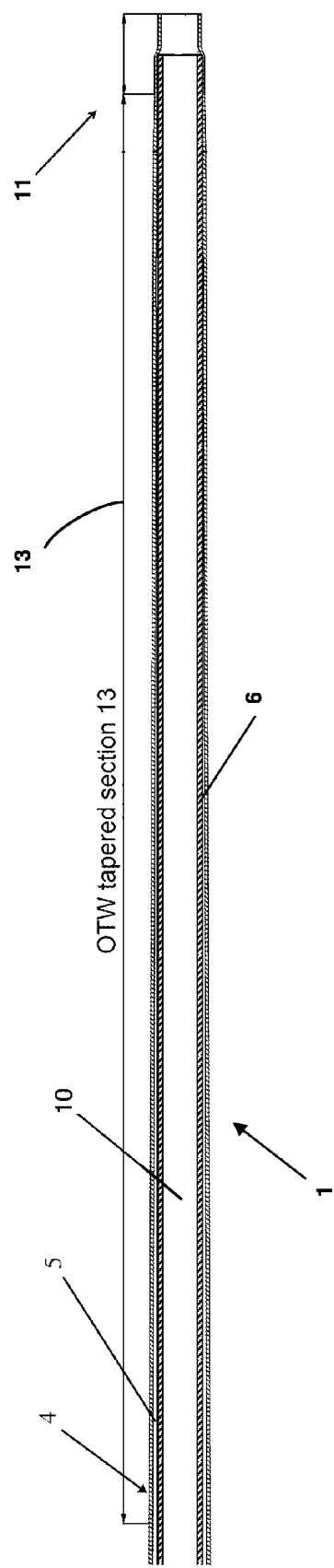
FIG. 3 is a side cutaway view of a distal portion of the device of the embodiment of FIG. 1.

Examples of over-the-wire (OTW) embodiments of the device are shown in FIGS. 1 to 7. With reference to FIG. 1, an elongated dilation device is shown, of which most of the length of the dilation device is comprised of a usable length 7. The usable length 7 of the device in the embodiment of FIG. 1 is from hub 3 to the device distal tip. The usable length 7 does not include the portion of OTW shaft that is received inside of hub 3. The usable length 7 includes a distal end portion 11 and a proximal end portion 12 of the device (FIG. 1). As previously described, dilator 1 includes metallic shaft 6 and polymer sleeve 4 (FIG. 3). The flexibility of the shaft enables the dilator to traverse the tight bends of tortuous vasculature. In some embodiments, the usable length ranges from about 45 to 150 cm. A practitioner using the dilator advances or retracts the hub and shaft to advance or retract the distal end of the dilation device.

Referring to FIG. 5, some embodiments of the OTW dilation device comprise a metallic shaft 6 (a hypotube) made of stainless steel (e.g. 304 stainless steel), an inner polymer layer 4b' (typically PET shrink-wrap) covering a portion of the hypotube, an outer polymer layer 4a' comprised of a nylon, and a compressible layer 5 between metallic shaft 6 and outer polymer layer 4a'. Certain embodiments of the dilation device define a lumen 10 with a diameter that is generally slightly larger than the outer diameters (e.g. about 0.014, 0.018 or 0.035 inches i.e. about 0.36, 0.46, 0.89 mm) of conventional guide-wires with which it is to be used, so as to fittingly accommodate receipt of the guide-wire therethrough. Alternative embodiments of the dilation device define lumens that correspond with guide-wires of different diameters than the outer diameters of conventional guide-wires, to fit closely around such guide-wires.

FIG. 3 illustrates the distal portion of FIG. 1. It shows polymer sleeve 4 gradually decreasing in thickness towards the distal end of dilator 1 in tapered section 13 to contribute to a distal decrease in overall outer diameter (i.e. an outer diameter taper) of dilator 1. In one example of an OTW dilator, metallic shaft 6 (e.g. a hypotube) has a constant wall thickness of about 0.0025 inches (about 0.06 mm) from distal end portion 11 to proximal end portion 12 while the thickness of polymer sleeve 4 (e.g. a nylon) ranges from about 0.005 inches (about 0.12 mm) at the proximal end portion 12 of the shaft of dilator 1 to about 0.0035 inches (about 0.089 mm) for the most distal 1 inch (about 25.4 mm) of the shaft of dilator 1. In alternate embodiments, the overall diameter of dilator 1 further increases proximally through an increase in the radial dimension (thickness) of a compressible layer 5, as shown in the embodiments of FIGS. 3 and 5 over the length of tapered section 13. As previously emphasized, the proximal increase in overall diameter (or distal decrease) of the dilator allows it to present a tapered surface to force away portions of a lesion surrounding an inserted guide-wire away from the guide-wire as device is advanced.

Figure 6:
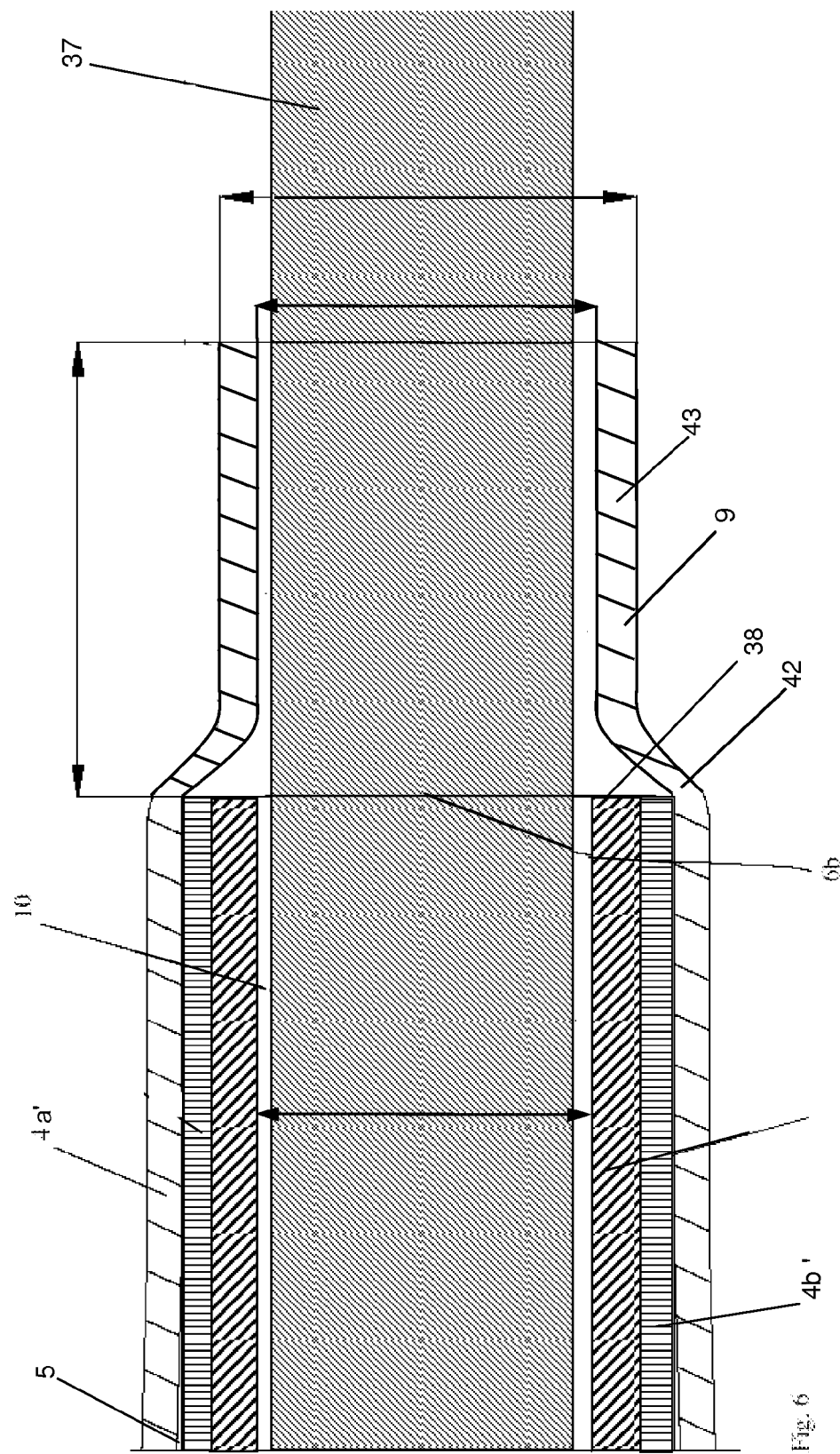
FIG. 6 is an enlarged view of the distal portion of the dilator of FIG. 5 with a received guide-wire.
Figure 7:
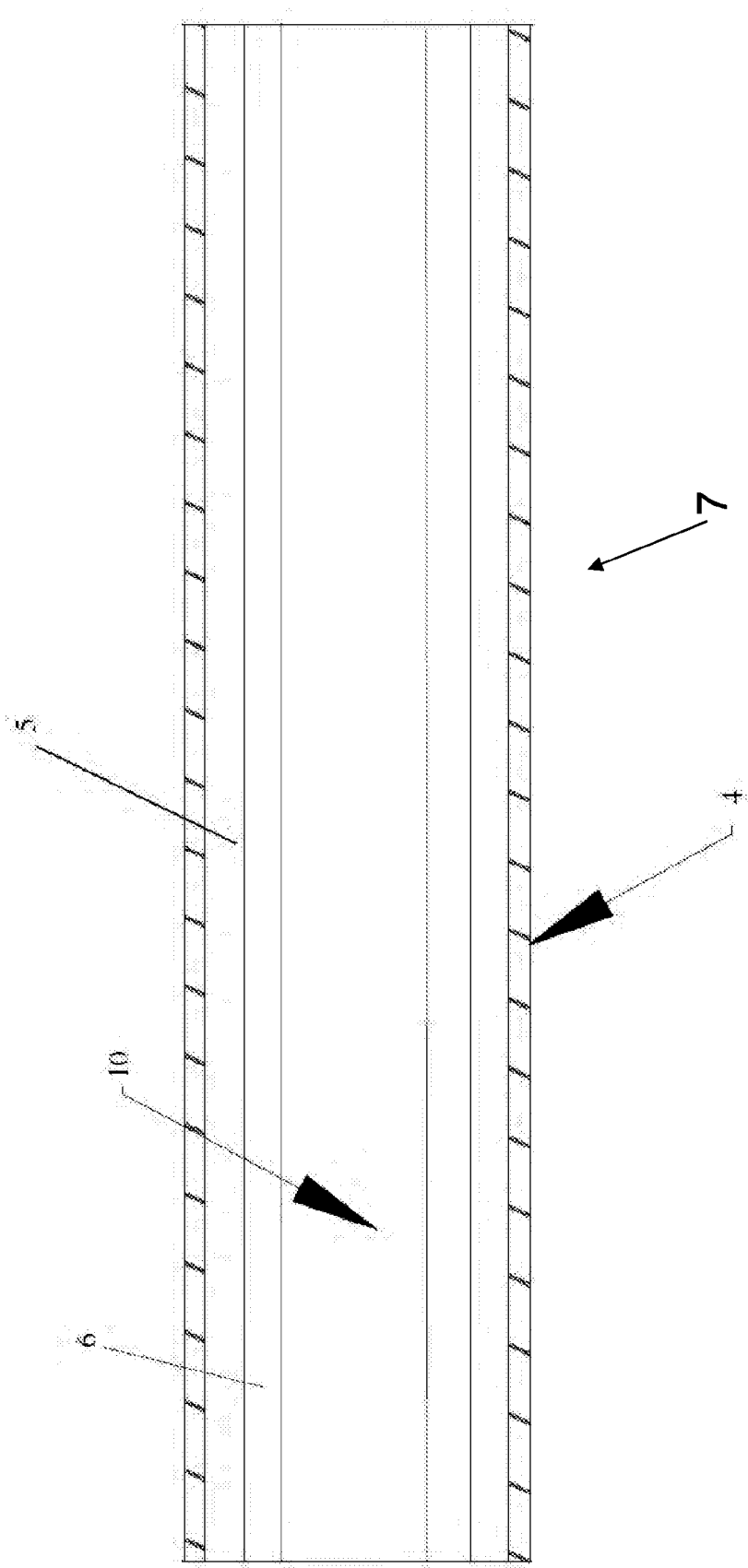
FIG. 7 shows an enlarged view of a middle portion of the dilator shaft of FIG. 1.

Examples of the distal tapers of OTW embodiments include polymer distal tip taper 42 of FIG. 6, and tapered section 13 of FIG. 3. In some embodiments, tapered section 13 of FIG. 3 is a gradual taper of about 3-5 inches, more specifically about 4 inches (about 101.6 mm), in length. Having dilator 1 taper gradually over a longer distance can help reduce the amount of force needed to advance the device. In some embodiments, a hydrophilic coated section 2 of dilator 1 (FIG. 1) can reduce the friction at distal end portion 11 and consequently aid in crossing a lesion. In some such embodiments, hydrophilic coated section 2 comprises primer coat 2-TS-96 and top coat 3-TS-12 manufactured by Hydromer Inc. A suitable hydrophilic coating is lubricous when it is wet, such as when in a patient, but the coating does not need to be lubricous when outside of a patient (and dry).

The embodiment of FIG. 5 also includes helical cut 35 along metallic shaft 6. Helical cut 35 increases flexibility over the cut length for navigating to a treatment site. The term "cut length" refers to the length of a tube that is cut into. For example, a "cut length of 5 cm" refers to the cut being made along a 5 cm long portion of metallic shaft 6. The cut lengths of different embodiments of metallic shaft 6 include, but are not limited to, about 6, 12 or 103 cm (about 2.4, 4.7 or 40.6 inches, respectively) as described further hereinbelow. In typical embodiments of the dilation device, the helical cut does not extend to the distal end 6b of metallic shaft 6 (FIG. 5) such that end surface 38 (FIG. 6) does not have any sharp edges i.e. helical cut 35 is not cut into the most distal end surface of the metallic shaft. In further alternative embodiments, metallic shaft 6 may have one or more cuts that have a shape other than helical, for example circular cuts, dove-tail cuts or C-cuts.

In the embodiment of FIG. 5, outer polymer layer 4a' extends beyond distal end 6b of metallic shaft 6 to form polymer distal tip 9. In some examples, polymer distal tip 9 extends about 0.5 mm (approximately 0.02 inches) beyond distal end 6b of metallic shaft 6. The FIG. 6 embodiment illustrates polymer distal tip 9 reducing in diameter at polymer distal tip taper 42 to form narrow portion 43. Guide-wire 37 is fittingly received by lumen 10 and narrow portion 43 of polymer distal tip 9. The device is designed to fit closely over an installed guide-wire and be advanced over the guide-wire so that the tapered surface (i.e. the tapered distal end) of the device pushes tissue away from the guide-wire and thereby compresses the occlusive tissue against the vessel wall. The relatively larger inner diameter of the metallic shaft enables the dilator to travel over the guide-wire with less friction than if the metallic shaft inner diameter were the same as the polymer tip's inner diameter, thereby reducing the amount of force needed to be applied to the proximal end of the dilator for advancement.

Figure 4B:
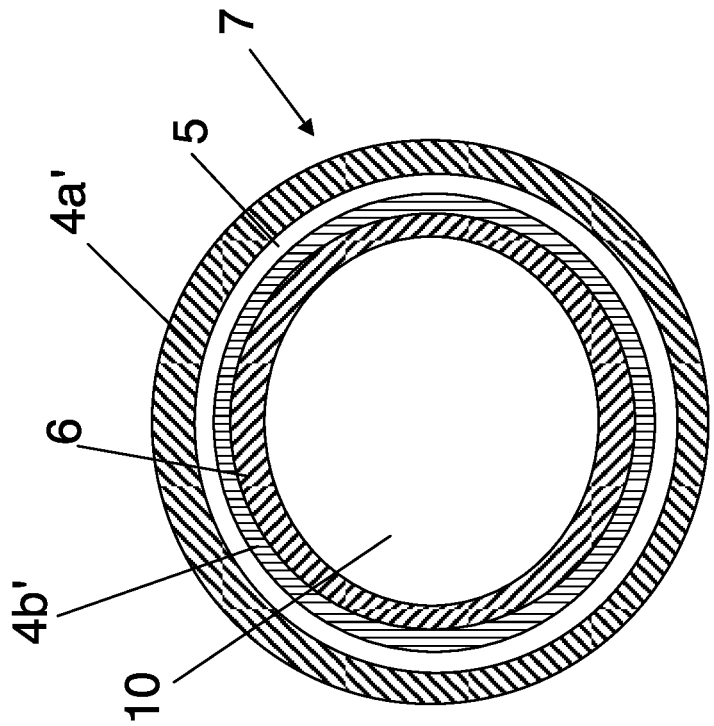
FIG. 4b is a cross section of the OTW dilator shaft at line 4b-4b of FIG. 5 near the distal end.
Figure 4A:
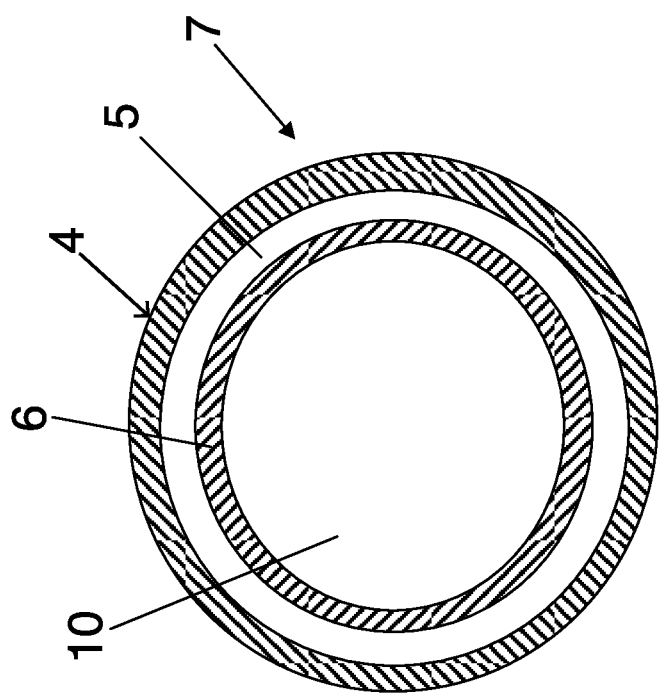
FIG. 4a is a cross section of the usable length of the OTW dilator shaft at line 4a-4a of FIG. 2 near the proximal end of the usable length of the OTW dilator shaft.

The embodiment of FIG. 4a shows a cross section at a proximal location of the usable length 7 of dilator 1 as indicated by FIG. 2 line 4a-4a. The example of FIG. 4a includes: lumen 10, which has a diameter of about 0.0375±0.001 inches (about 1.0±0.03 mm), defined by the inner surface of metallic shaft 6; metallic shaft 6 (typically a hypotube) which has an outer diameter of about 0.0425±0.0005 inches (about 1.1±0.01 mm); compressible layer 5 which has an outer diameter of about 0.057±0.0015 inches (about 1.5±0.04 mm); and polymer sleeve 4 which has an outer diameter of about 0.065 inches (about 1.7±0.03 mm). The dimensions of alternative embodiments are not limited to the above dimensions and substitutions of material are possible. Some embodiments include shaft 6 being comprised of 304 stainless steel and/or polymer sleeve 4 being comprised of nylon. Materials suitable for compressible layer 5 may include (but are not limited to) fluids, gels, compressible elastic materials and other materials that yield easily to pressure i.e. are compliant. The yieldability of compressible layer 5 contributes to the flexibility of the usable length of dilator 1 and allows for a slight deformation of polymer sleeve 4 when bending.

The embodiment of FIG. 4b shows a cross section of distal end portion 11 of dilator 1 at the location indicated by line 4b-4b of FIG. 5. The cross section of the shaft of dilator 1 at this distal location is similar to the proximal cross section shown in FIG. 4a, with the addition of inner polymer layer 4b' on the outer surface of the distal portion of metallic shaft 6 for covering one or more cuts (e.g. helical cut 35) made into or through metallic shaft 6. Inner polymer layer 4b' may be comprised of PET heat-shrink tubing or other suitable materials, and in some examples is a PET layer having a thickness of about 0.001 inches (about 0.03 mm). The thickness of outer polymer layer 4a' varies (i.e. tapers), decreasing toward the distal tip of dilator 1, and in the location illustrated in the embodiment of FIG. 4b, may have a thickness of about 0.0035 inches (about 0.089 mm). In some embodiments of dilator 1, metallic shaft 6 is comprised of number 304 stainless steel and outer polymer layer 4a' is comprised of nylon. Dilator 1 increases in overall outer diameter from distal line 4b-4b to proximal line 4a-4a to thereby allow the disclosed dilation device to force away portions of a lesion away from a traversing guide-wire as the dilation device is advanced.

The examples of the dilation device listed below can help provide access to the indicated sites but can also be used to provide access to other sites and are not limited to the particular applications listed. In some examples, an OTW device with a usable length of about 75 cm (~29.5 inches) and a 12 cm (~4.7 inches) or a 6 cm (~2.4 inches) distal cut length could provide ipsilateral access to a leg vessel. In another example, a device with a usable length of about 115 cm (~45.3 inches) and a 103 cm (~40.6 inches) distal cut length could provide contralateral access to a leg vessel.

The embodiment of FIG. 5 illustrates an intermediate marker 8 (between the ends of the device) that in some embodiments is radiopaque. Intermediate marker 8 may be comprised of: gold, platinum, iridium, palladium, rhodium, or a combination of these or similar materials. Alternative embodiments of dilator 1 include a radiopaque marker at the tip of distal end portion 11, with additional markers placed at regular intervals from the tip, e.g. every 10 mm (about 0.39 inches), for visualizing, measuring or positioning.

Some OTW embodiments have a curved distal end wherein different angles, shapes and curve lengths are possible. Some examples having a curved distal end include one or more radiopaque markers to aid in guiding, steering and positioning.

Monorail

FIGS. 8 to 17 illustrate monorail embodiments of the dilation device.

Monorail embodiments of the dilation device are primarily intended for coronary procedures but some monorail embodiments may be used for peripheral procedures. Details of several such embodiments follow.

Figure 8:
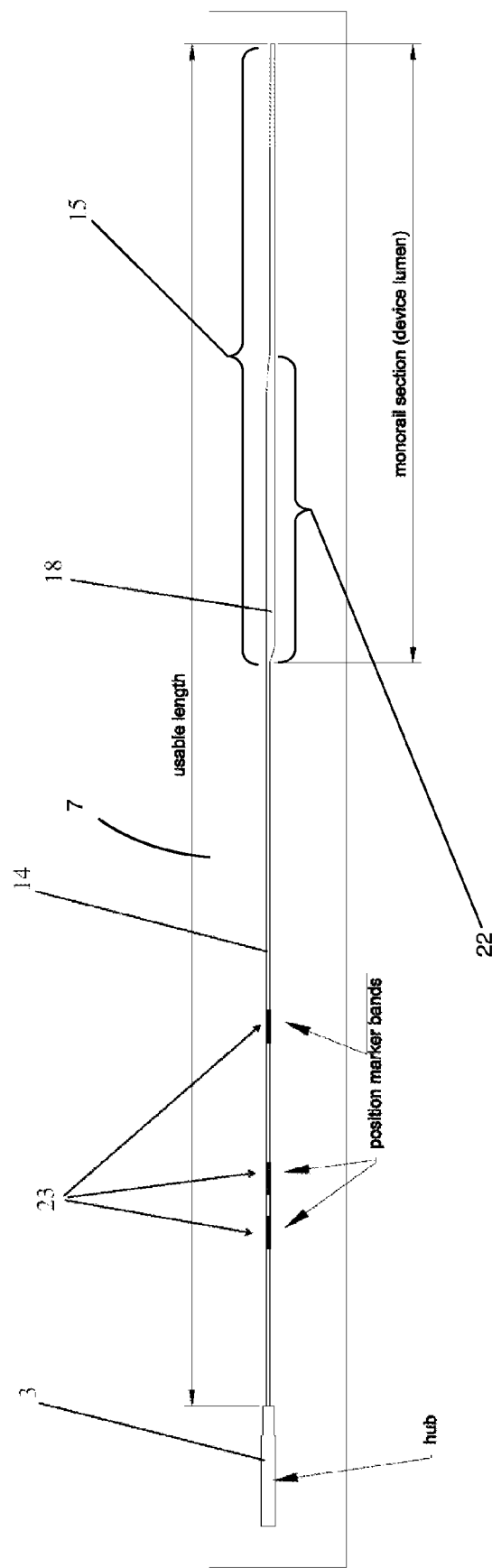
FIG. 8 illustrates a full assembly of a monorail embodiment of the dilation device.

Referring to FIG. 8, monorail embodiments of the dilation device comprise a proximal shaft 14 that is coupled to a hub 3 at its proximal end and to a monorail section 15 at its distal end. The proximal shaft comprises a pusher wire 17, typically made of stainless steel (e.g. 304 stainless steel), and covered by polymer sleeve 4, which is comprised of at least one polymer layer. The monorail section has a lumen 10 for receiving a guide-wire 37. A practitioner can manipulate the hub 3 and proximal shaft 14 to advance or retract the distal end of the dilation device. The distance from hub 3 to monorail section distal end 41 (FIG. 12) is referred to as the usable length 7 i.e. the part of the dilator which is distal of the hub. Examples of the usable length 7 includes lengths of about 145 cm (~57.1 inches) and about 150 cm (~59.1 inches), but the usable length is not limited to the aforementioned lengths. Position markers 23 (FIG. 8) on proximal shaft 14 can be used for positioning and to measure the distance the device is inserted into a patient.

Figure 9:
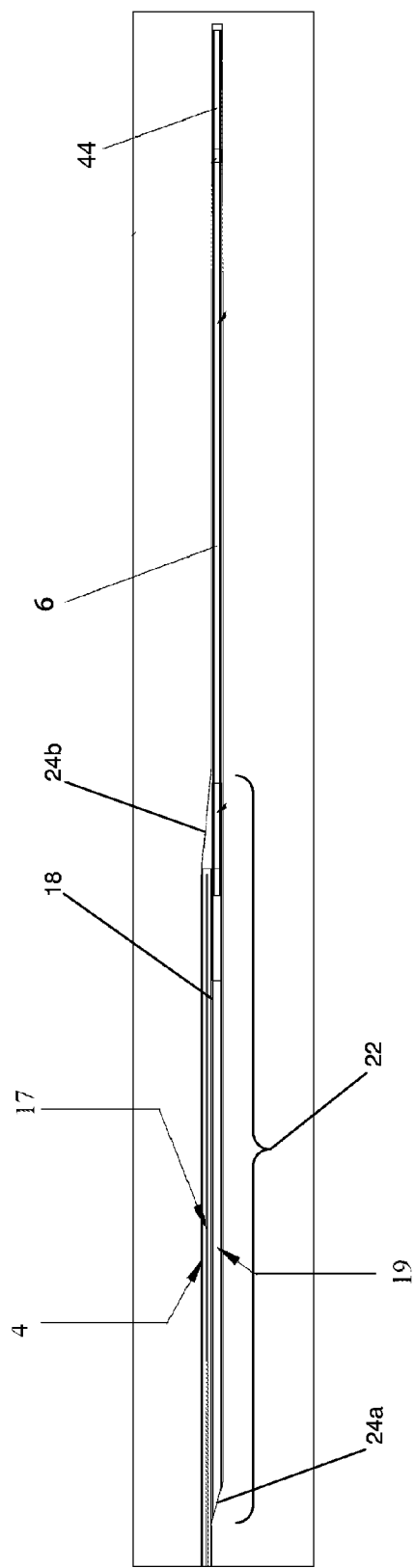
FIG. 9 is an enlarged view of the monorail section of the embodiment of FIG. 8 including the distal portion of the proximal shaft that is joined thereto.

FIG. 9 is an enlarged view of monorail section 15 of the embodiment of FIG. 8. In typical monorail embodiments, monorail proximal portion 19 of the monorail section 15 and the proximal shaft 14 (FIG. 8) are overlapping and attached together by a lap joint 18 to form an overlapping portion 22. Overlapping portion 22 can also be referred to as the bonded portion of the device. Overlapping portion 22 typically includes sloped surfaces 24a and 24b (FIG. 9) for reducing friction when inserting and removing the dilation device. The embodiment of FIG. 12 includes a sloped surface 24b which is defined by a polymer layer and which overlaps metallic shaft 6.

Figure 10:
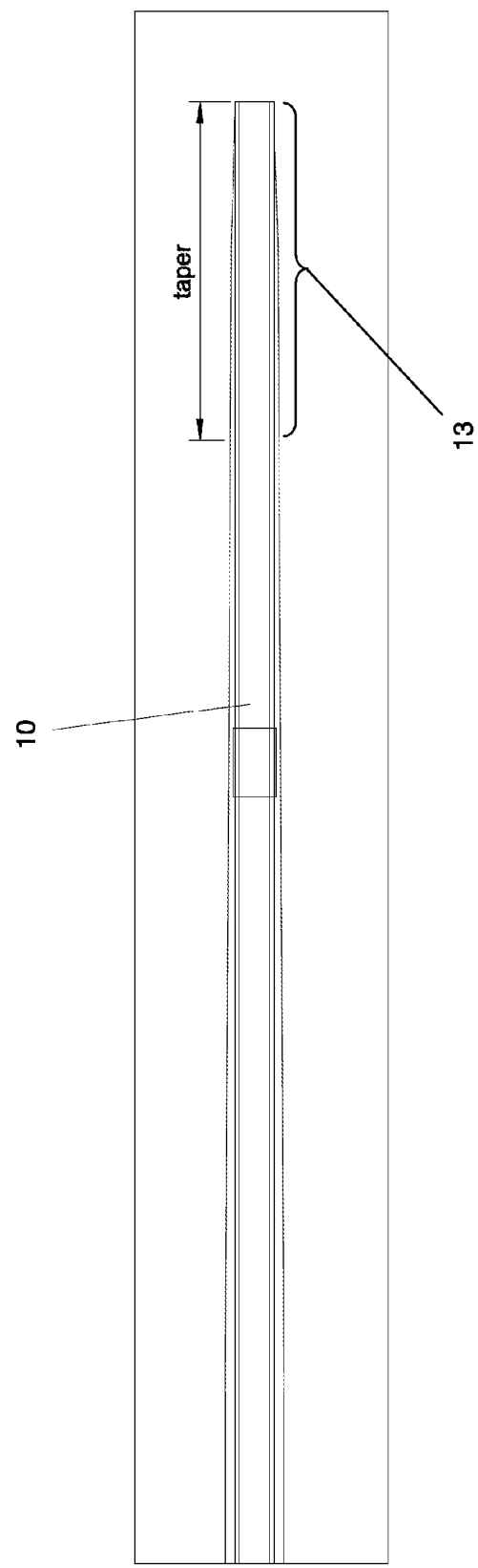
FIG. 10 is an enlarged view of a distal portion of FIG. 9.
Figure 11:
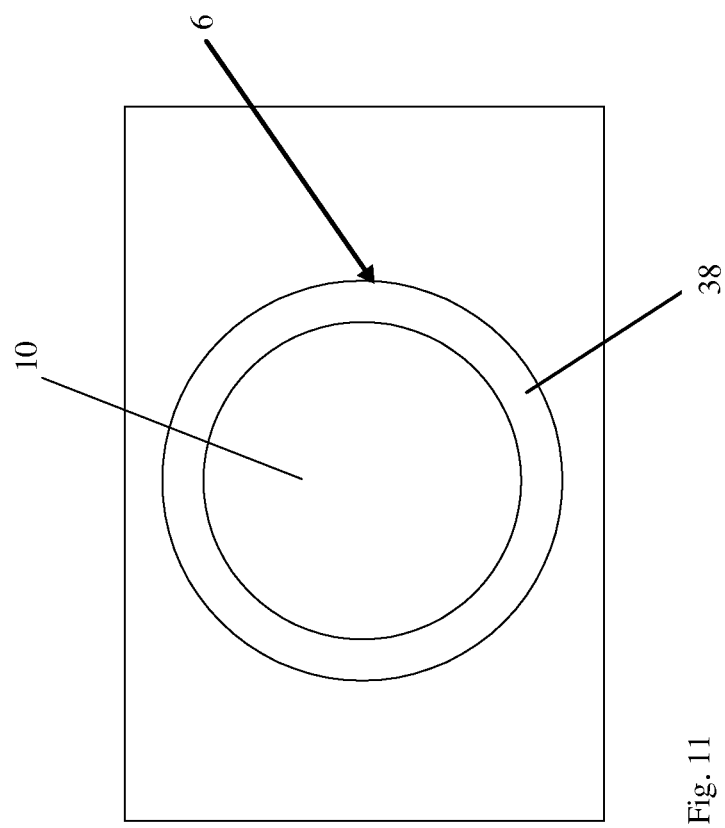
FIG. 11 is an enlarged end view of the tip of the embodiment of FIG. 10.

FIG. 10 is an enlarged view of a distal portion of FIG. 9. In typical embodiments of the device, monorail distal portion 44 (FIGS. 9, 13) of monorail section 15 decreases in outer diameter distally to form a taper, shown in FIG. 10 as tapered section 13. The embodiment of FIG. 10 has a relatively more gradual tapered section 13 than does the embodiment of FIG. 12. Different embodiments of the device have different taper lengths. In some embodiments, tapered section 13 ranges from about 4 mm (about 0.16 inches) to about 15 mm (about 0.60 inches) in length.

Figure 12:
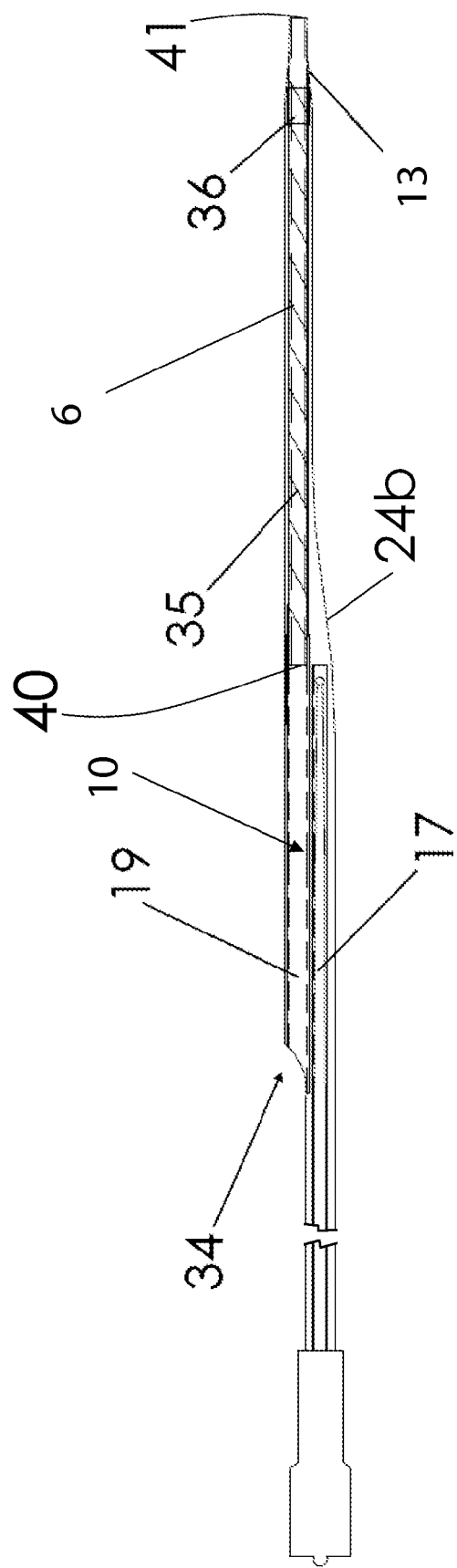
FIG. 12 shows a side cutaway view of another monorail embodiment of the device.

FIG. 12 shows a side cutaway view of another monorail embodiment of dilator 1. Longitudinally aligned metallic shaft 6 and monorail proximal portion 19 define lumen 10. The distal end of monorail proximal portion 19 abuts and is joined to the metallic shaft proximal end 40. Lumen 10 has a proximal lumen opening 34 at the proximal end of monorail proximal portion 19 and a distal lumen opening 33 at monorail section distal end 41. In some monorail embodiments, metallic shaft 6 has an inner diameter of about 0.018 inches (about 0.4 mm) and an outer diameter of about 0.022 inches (about 0.5 mm).

As discussed above, some embodiments include metallic shaft 6 being comprised of, for example, nitinol. In typical monorail embodiments (e.g. FIG. 12), a selected length of the distal portion of metallic shaft 6 includes a helical cut 35 through the metallic shaft sidewall, possibly created using a laser. Any portions of metallic shaft 6 that are not cut through (or into) are relatively rigid in comparison to monorail proximal portion 19, but can flex for navigation of the dilation device around bends or other tortuous anatomy. While the embodiment of FIG. 12 discloses a helical cut substantially along the entire length of metallic shaft 6, in alternative embodiments the helical extends along only a portion of metallic shaft 6. Typically, the end surface 38 (FIG. 11) of metallic shaft 6 is not cut into.

The flexibility of the distal portion of metallic shaft 6 depends on, in part, the cut length of the tube and the pitch (distance between cuts). The pitch can vary along a single device: for example, it is possible to decrease the pitch along the length of metallic shaft 6 to have a smaller pitch closer to the distal end tip to increase flexibility closer to the tip. In one specific example, metallic shaft 6 has a 15 cm (~5.9 inches) distal helical cut with a distal part of the helical cut having a pitch of about 1.75 mm (~0.069 inches) and a proximal part of the helical having a pitch of about 2.75 mm (~0.108 inches). Another example includes the helical cut with a distal part having a pitch of about 1.00 mm (~0.039 inches) and a proximal part having a pitch of about 2.00 mm (~0.078 inches). Alternative embodiments comprise cuts with other shapes such as, for example, C-shaped cuts and/or dove-tail cuts. In some examples, the cuts do not go all the way through the material of metallic shaft 6.

As illustrated in FIG. 12, a monorail section 15 can also include a radiopaque distal end marker 36 for imaging.

Figure 13:
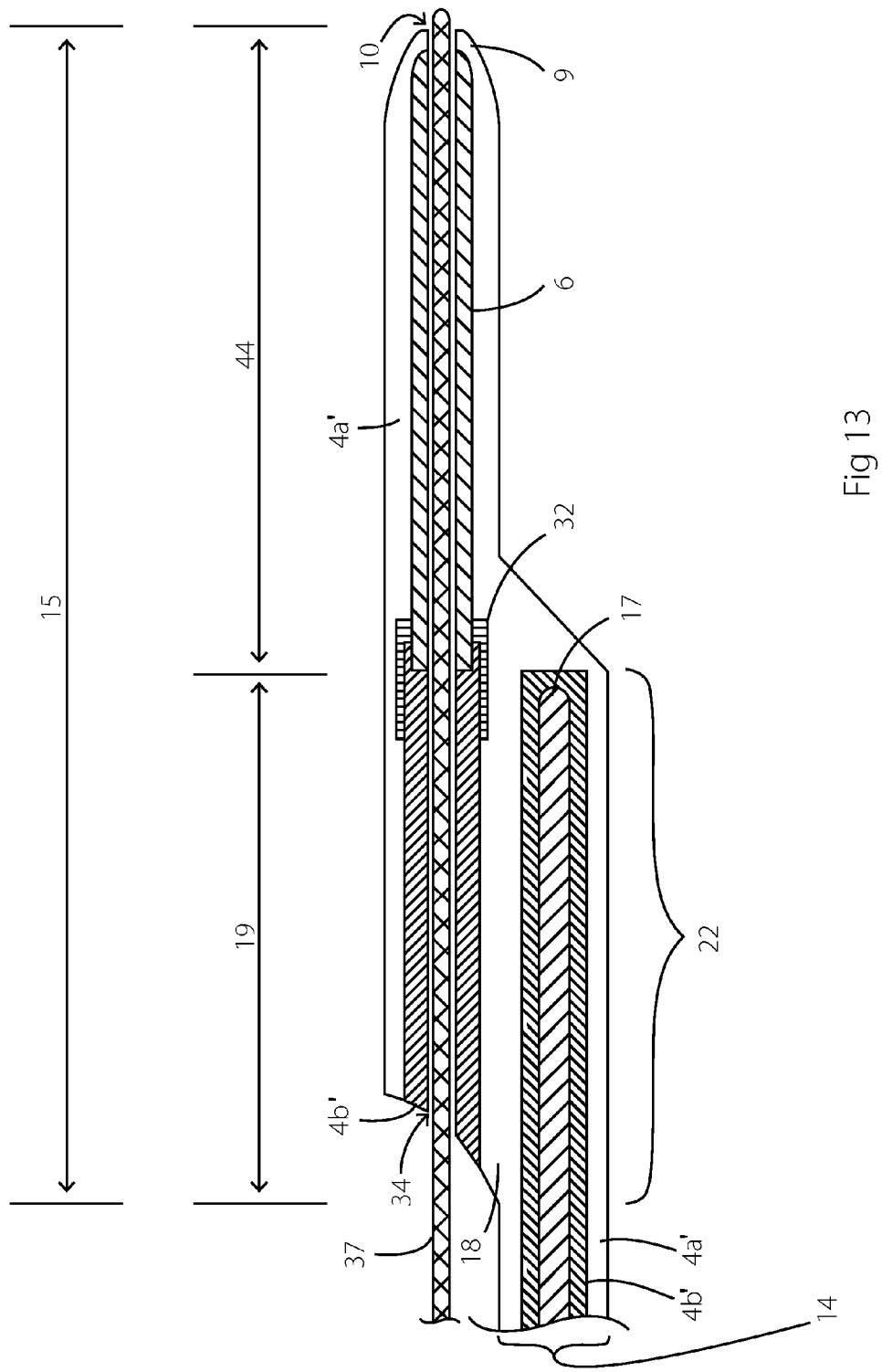
FIG. 13 shows a side cutaway view of the monorail section of another monorail embodiment of the device.

FIG. 13 shows a side cutaway view of another monorail embodiment of the device including further details of construction. In this embodiment, monorail section 15 includes lumen 10 passing through both monorail distal portion 44 and monorail proximal portion 19. Lumen 10 has a guide-wire 37 received therein. Monorail distal portion 44 includes metallic shaft 6 and covered by polymer sleeve 4. Metallic shaft 6 is typically comprised of a metal tube, for example a nitinol tube. In a particular example of the monorail section 15, the distal portion of the monorail lumen is defined by a metallic shaft 6 (e.g. a nitinol tube) that is covered by a PET inner polymer layer (not shown in drawing) which in turn is covered by an outer polymer layer 4a' (a Pebax® layer about 0.00325 inches or about 0.083 mm thick).

Typically, monorail proximal portion 19 does not include a metal tube but is comprised of flexible materials (i.e. materials which are relatively flexible in comparison to a solid metal) and which define a proximal portion of guide-wire receiving lumen 10. Referring to the embodiment of FIG. 13, monorail proximal portion 19 (the proximal portion of the monorail section) is primarily comprised of two layers of polymer, an inner polymer layer 4b' of polyimide tubing and an outer polymer layer 4a' of Pebax®, with the inner polymer layer 4b' defining the corresponding portion of guide-wire receiving lumen 10. Inner polymer layer 4b' and metallic shaft 6 are coaxially aligned, with a distal portion of inner polymer layer 4b' overlapping metallic shaft 6, and the overlap being enclosed by a PET heat shrink 32. In typical embodiments, inner polymer layer 4b' and metallic shaft 6 have substantially identical (i.e. similar or the same) inner diameters for receiving the corresponding guide-wire.

The embodiment of monorail section 15 of FIG. 13 also includes the polymer sleeve 4 extending beyond the end of metallic shaft 6 to define a leading polymer distal tip 9 with a distally decreasing outer diameter, in a manner similar to the previously described OTW embodiments, and which functions to force away material from a corresponding guide-wire in the manner described previously.

In one example, the proximal portion of the monorail lumen 10 is defined by a monorail proximal portion 19 which includes a polyimide inner polymer layer 4b', about 0.0010 inches (about 0.03 mm) thick, which is covered by Pebax® outer polymer layer 4a''. The Pebax® layer also covers metallic shaft 6 (a nitinol tube). In some examples, the thickness of the Pebax® layer varies (i.e. tapers) along the length of monorail section 15. The polyimide layer of monorail proximal portion 19 overlaps the proximal portion of metallic shaft 6. The overlap is covered and joined together by a layer of PET heat shrink 32 about 0.0005 inches (about 0.01 mm) thick (see FIG. 13). There is a thin compressible layer (not shown in FIG. 13) between the Pebax® outer polymer layer 4a' and the polyimide inner polymer layer 4b'. At the distal tip of monorail section 15, the thickness of the Pebax® layer that covers the nitinol tube reduces to about 0.002 inches (about 0.05 mm). The most distal 20 cm (~7.9 inches) of the monorail section 15 is covered with a hydrophilic coating.

In some embodiments, monorail section 15 has a length of about 20 to 30 cm (~7.9-11.8 inches), while in one specific embodiment, monorail section 15 has a length of about 30±0.5 cm (~11.8±0.2 inches).

The embodiment of FIG. 13 illustrates lap joint 18 of overlapping portion 22 joining monorail proximal portion 19 of the monorail section 15 with proximal shaft 14 (which contains pusher wire 17) such that there is substantially one metal support element at any given point along the usable length of the dilation device (pusher wire 17 proximally and metallic shaft 6 distally). Embodiments of the dilation device having this configuration may provide flexibility for navigating to a treatment site by avoiding having parallel metal support elements that create excess rigidity, while also providing sufficient pushability/stiffness for crossing the occlusion or stenosis by substantially having a metal support element for entire usable length of the dilator.

Some embodiments of the monorail dilation device having a lumen 10 with a diameter of about 0.015 to about 0.018 inches (about 0.38 to about 0.46 mm) are suitable to provide a sufficiently close fit for use as a dilator with a guide-wire with a diameter of about 0.014 inches (about 0.36 mm). Other embodiments of the dilation device have a larger diameter lumen 10 for use with a larger diameter guide-wire. To reduce friction between lumen 10 and guide-wire 37, some embodiments include a thin layer of polymer (not shown in drawings) on the inside surface of the metallic shaft.

Figure 14A:
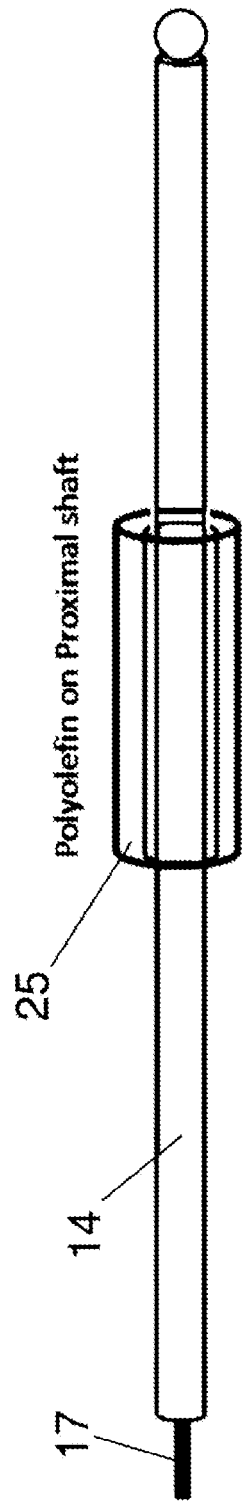
FIGS. 14a to 14c show the stages of constructing an embodiment of a hub of the dilation device.
Figure 14B:
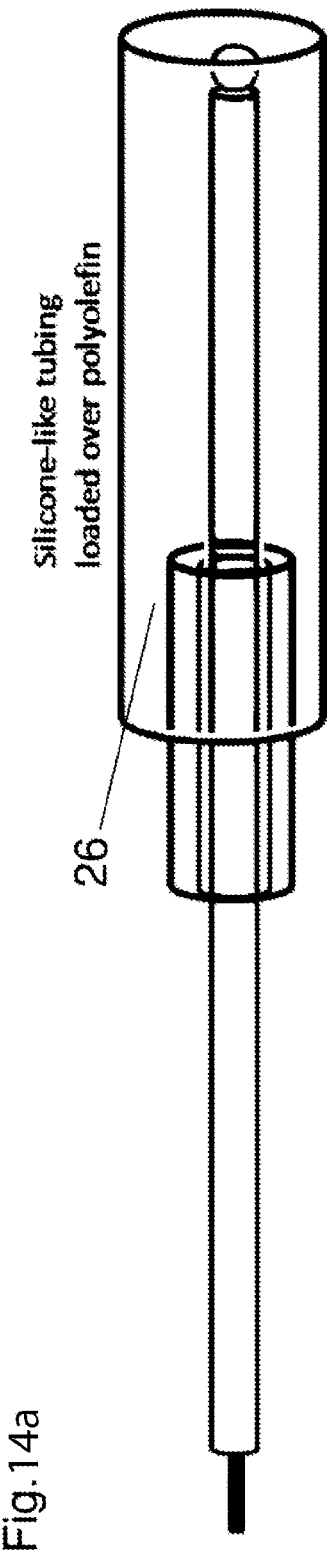
Figure 14C:
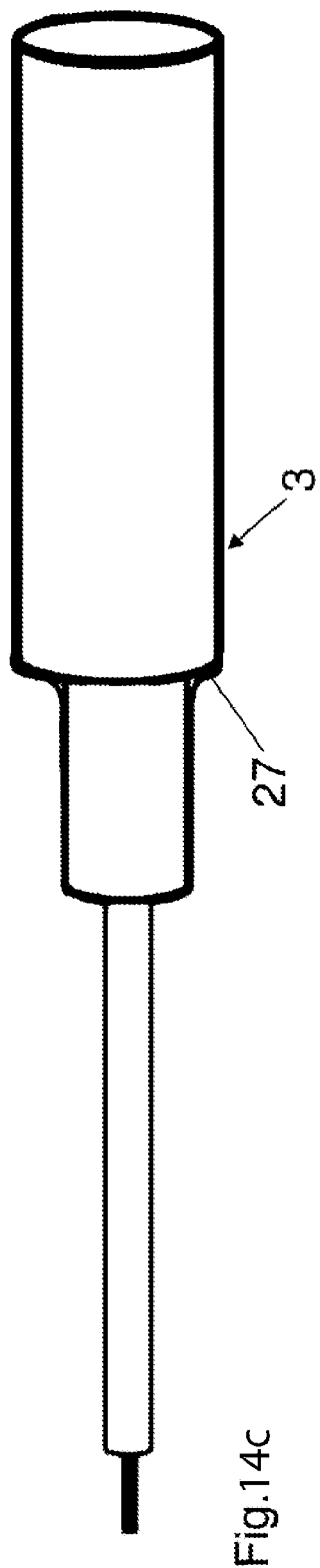

The proximal end of the proximal shaft 14 and hub 3 can be joined together by a friction joint, by an adhesive or by some other means. In the embodiment of FIGS. 14a to 14c, hub 3 is comprised of silicone-like tubing 26 and is joined to proximal shaft 14 by a friction joint comprising polyolefin tubing 25. Hub 3 is covered by a polyolefin label 27 which can be used for identification purposes. In some examples, polyolefin label 27 also covers polyolefin tubing 25 and/or a portion of proximal shaft 14.

FIGS. 15a and 15b illustrate the construction of an embodiment of the proximal shaft 14 comprising a 304 stainless steel pusher wire 17 covered by an inner polymer layer 4b' (proximal shaft polyimide tubing), which is then covered by outer polymer layer 4a' (proximal shaft Pebax® tubing). A specific embodiment of proximal shaft 14 comprises a stainless steel pusher wire 17 that has a proximal diameter of about 0.022 inches (about 0.56 mm) and a distal diameter of about 0.045 inches (about 1.1 mm). The pusher wire 17 is covered by a 0.001 inch (about 0.025 mm) thick polyimide inner polymer layer 4b' which is then covered by a 0.002 inch (about 0.051 mm) thick Pebax® outer polymer layer 4a'. In some examples, the outer surface of the proximal shaft 14 has one or more PET markers thereupon. In one specific example, the pusher wire 17 is about 53 inches long (about 1346 mm), including the part of the pusher wire inside of the hub 3, and the most distal 7 inches (about 178 mm) of pusher wire 17 are tapered. In one specific example the hub is about 5 cm (~2 inches) long and the pusher wire extends almost to the proximal end of the hub. The disclosed embodiments of the pusher wire are sufficiently flexible to be able to navigate through tortuous vasculature.

Figure 16:
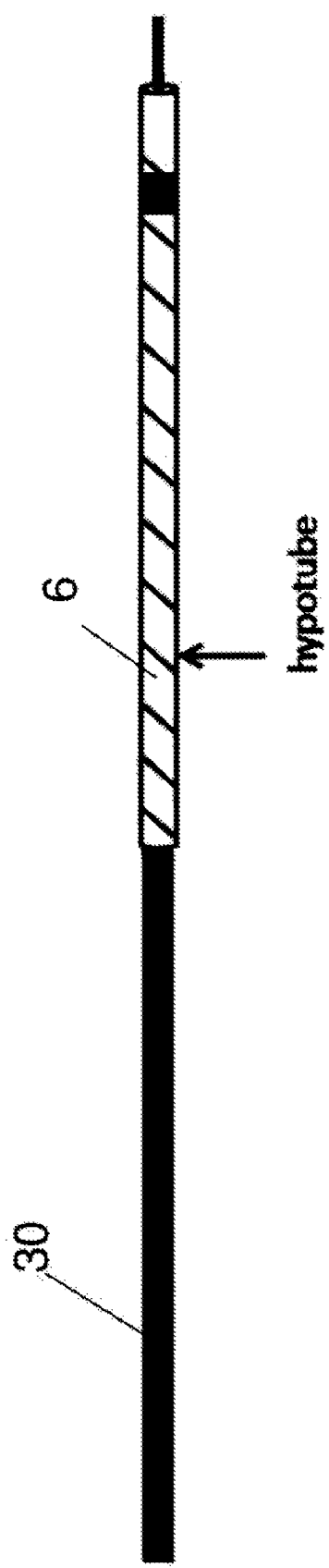
FIG. 16 shows a monorail inner tube and a mandrel.
Figure 17A:
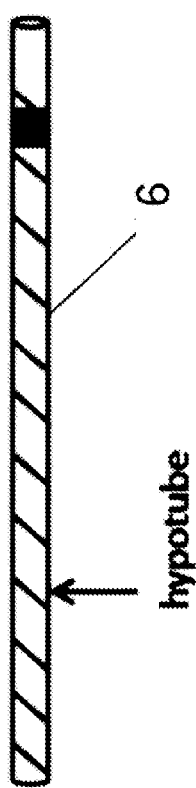
FIGS. 17a to 17d show the stages of constructing an embodiment of a monorail section.
Figure 17B:
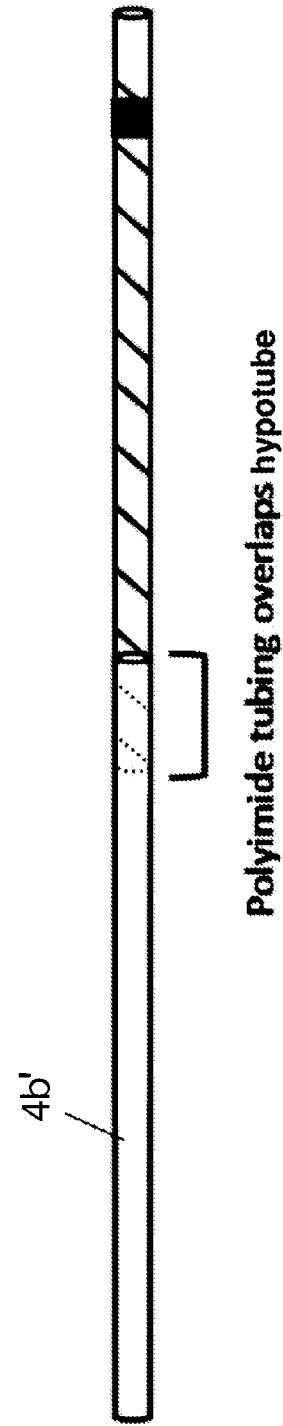
Figure 17C:
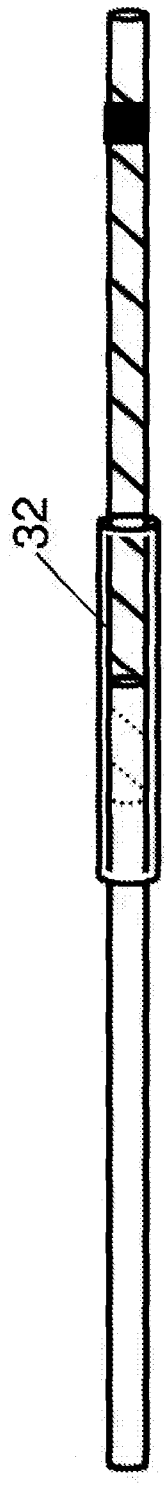
Figure 17D:
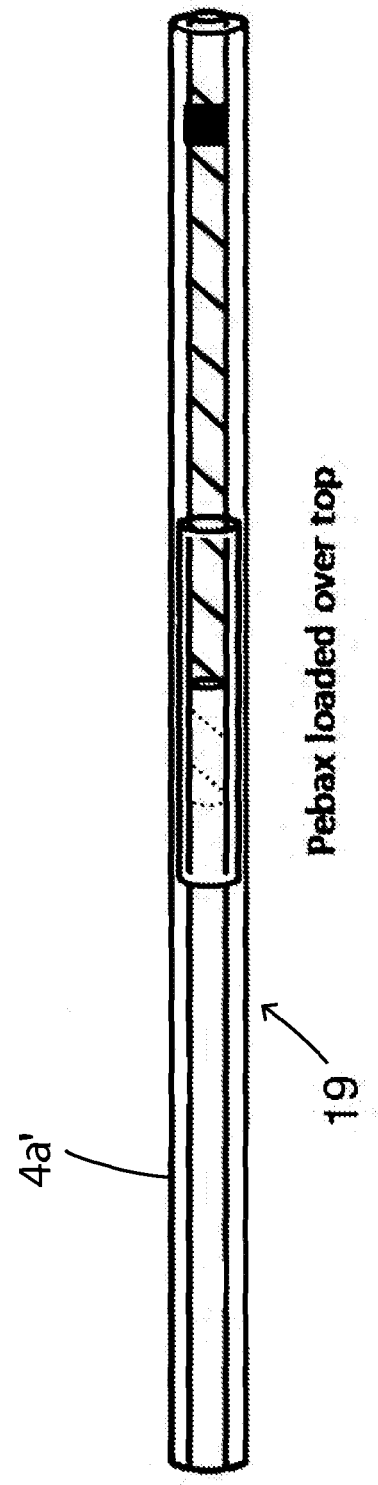

FIGS. 16 and 17 illustrate the construction of an embodiment of monorail section 15 around a mandrel 30. Mandrel 30 is shown in FIG. 16 partially covered by a nitinol hypotube (metallic shaft 6). FIGS. 17a to 17d show the steps of assembling materials around the mandrel 30 but mandrel 30 is not shown. First, a metallic shaft 6 (a nitinol hypotube) is loaded onto the mandrel (FIG. 17a). Next, as shown in FIG. 17b, an inner polymer layer 4b' (polyimide tubing) is then installed such that an end portion of it overlaps with an end portion of metallic shaft 6. The adjoining portions of the polyimide tubing and metallic shaft 16, including the overlap, are covered with and joined by PET heat shrink 32 (FIG. 17c). Finally, substantially all of the polyimide tubing and metallic shaft 6 are covered with outer polymer layer 4a' (Pebax®) (FIG. 17d). In alternative embodiments, other polymers/materials may be substituted for the polymers described in the embodiment of FIGS. 16 and 17, and other metals may be substituted for nitinol.

Method and Uses

In general use, a guide-wire is advanced through an artery and advanced through a lesion to be treated. The tapered distal tip of the dilation device is advanced over the guide-wire and is itself advanced at least partially across the lesion. This device can be used to make the lesion less resistant to crossing in subsequent operations, e.g. balloon crossing or stent installation.

Some embodiments of a method for treating an occlusion or stenosis of a vessel/artery using a dilation device include the steps of crossing the occlusion or stenosis with a guide-wire, followed by advancing a dilation device received on the wire over the guide wire to a proximal side of the occlusion or stenosis, and advancing the device into the occlusion or stenosis to a distal side of the occlusion or stenosis so as to push aside (without substantial cutting or scraping) at least a portion thereof so as to dilate a channel through the occlusion or stenosis that contains the guide-wire. The dilation device includes an inner diameter at its distal end that fittingly corresponds with the guide-wire and a tapered distal tip whereby the dilation device functions more like a wedge than a cutting or scraping device. Some embodiments further include the step of the dilation device being withdrawn, followed by the installation of an angioplasty balloon catheter, a stent catheter or some other device. If necessary, progressively larger diameter dilation devices can be advanced across the stenosis until it is possible to cross the lesion with the balloon angioplasty catheter or stent catheter or other device. In some embodiments the vessel is a coronary artery, while in some other embodiments the vessel is a peripheral artery.

An embodiment of a method of preparing a crossable arterial occlusion or stenosis for balloon angioplasty (or other vessel repair procedures) using monorail embodiments of the device includes the steps of: (a) crossing the occlusion or stenosis by inserting a guide-wire of a monorail delivery system through a passage of the occlusion or stenosis; (b) mounting a device having a monorail section suitably dimensioned for use in the monorail delivery system onto the guide-wire, wherein an inner diameter at the distal end of the monorail section fittingly corresponds with the guide-wire and the monorail section includes a tapered distal tip; (c) delivering the monorail section to the proximal end of the occlusion or stenosis; and (d) pushing the monorail section along the guide-wire through the occlusion or stenosis so as to force away at least a portion of the occlusion or stenosis away from the guide-wire so as to increase the diameter of the passage crossing through the occlusion or stenosis whereby the dilation device functions more like a wedge than a cutting or scraping device. This method can include a first device having a first distal monorail section having an outer diameter radially spaced a first distance from the center of the lumen, and the additional steps of (e) removing the first device having the first distal monorail section from the guide-wire; (f) mounting onto the guide-wire a second device having a second monorail section, the second monorail section having a larger outer diameter radially spaced a second distance from the center of the lumen thereof, and the second distance being greater than the first distance; and (g) repeating steps (c) and (d).

An embodiment of a method of preparing a crossable arterial occlusion or stenosis for balloon angioplasty (or other vessel repair procedures) using an OTW embodiment of the device includes: (a) crossing the occlusion or stenosis by inserting a guide-wire of an OTW delivery system through a passage of the occlusion or stenosis; (b) mounting a OTW device having a useable length suitably dimensioned for use in an OTW delivery system onto the guide-wire, wherein the dilation device includes an inner diameter at its distal end that fittingly corresponds with the guide-wire and a tapered distal tip; (c) delivering the OTW device to the proximal end of the occlusion or stenosis; and (d) pushing at least a portion of the useable length over the guide-wire through the occlusion or stenosis so as to force away at least a portion of the occlusion or stenosis away from the guide-wire so as to increase the diameter of the passage across the occlusion or stenosis whereby the dilation device functions more like a wedge than a cutting or scraping device. This method can include a first OTW device having a useable length with an outer diameter radially spaced a first distance from the center of the lumen, and the additional steps of (e) removing the first OTW device from the guide-wire; (f) mounting onto the guide-wire a second OTW device, the second OTW device having a useable length with a larger outer diameter radially spaced a second distance from the center of the lumen thereof, the second distance being greater than the first distance; and (g) repeating steps (c) and (d) to further dilate the channel.

Figure 18:
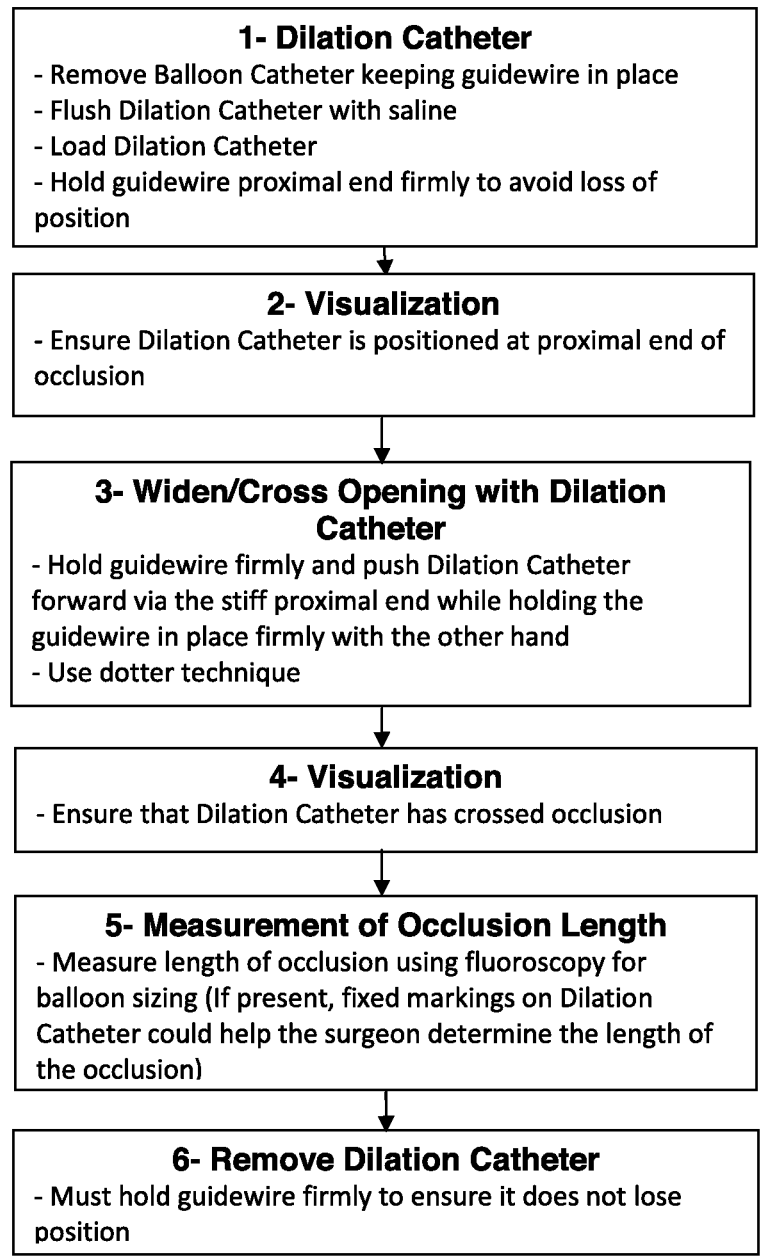
FIG. 18 shows the steps of a method of using the disclosed dilation device.

FIG. 18 shows an embodiment of a method of using the disclosed dilation device in an occlusion treatment. In step 1, the balloon catheter is removed and the dilation device is loaded onto the guide-wire and advanced towards the occlusion. Step 2 is to use visualization to ensure the dilation device is correctly positioned at the proximal end of the occlusion. In step 3, the dilation device is pushed forward to cross and widen the opening formed by the guide-wire. The Dotter technique of using multiple small forward movements (and small backwards movements as needed) can optionally be used. In some cases, rotation of OTW embodiments of the dilation device may be beneficial. Step 4 is to use visualization to confirm that the device has crossed the occlusion. In optional step 5, the occlusion length is measured for selection of balloon size. Step 6 is to remove the dilation device. The method of FIG. 18 could also be used to treat a stenosis.

Thus, embodiments of the present invention, including devices and methods, are usable for widening or dilating a channel containing a guide-wire in a treatment site. An elongated dilation device including a metal metallic shaft covered by a flexible layer, a tapered distal tip, and a lumen that fits closely to the guide-wire at the distal end of the dilator, is advanced over a guide-wire and through a treatment site to thereby function as a wedge to widen the channel.

The disclosed embodiments of a dilation device can be used in coronary arteries and in other sites where there are narrowings such as peripheral arteries, e.g., iliac, femoral or popliteal arteries, renal arteries, carotid arteries, vertebral arteries, or other narrowed tube-like structures such as ureters, fallopian tubes, urethras, esophageal strictures, bile ducts or narrowed arterial-venous grafts. Disclosed embodiments could also be used in venous structures, e.g. jugular veins, subclavian veins, and central venous structures. Some embodiments of the dilation device can possibly be used to widen vessels that have been previously treated e.g. vessels with covered stents, arterial-venous grafts in the heart, other grafts, dialysis tubing, or subclavian veins occluded due to pacemaker leads. Some embodiments of the dilation device could optionally be used for lead extraction, possibly by advancing the device over the lead to separate it from the surrounding tissue.

The embodiments of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination. As understood by one of average skill, some features described for OTW embodiments could be provided in monorail embodiments and some features described for monorail embodiments could be provided in OTW embodiments.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A dilation device installable on a guide-wire inserted through a vessel having a lesion therein, the dilation device comprising:
   a metallic shaft defining a lumen; and
   a polymer sleeve substantially covering the metallic shaft;
   a distal end of the dilation device being sized for fitting receipt of the guide-wire therethrough, the distal end defining a leading surface that is shaped to force away portions of the lesion surrounding the guide-wire away from the guide-wire as the distal end is advanced over the guide-wire through the lesion, whereby a channel through the lesion is at least partially dilated.

2. The dilation device of claim 1, wherein the leading surface is provided by the polymer sleeve.

3. The dilation device of claim 2, wherein an outer diameter of the polymer sleeve decreases distally to define an outer diameter taper.

4. The dilation device of claim 3, wherein the polymer sleeve extends distally beyond a distal end of the metallic shaft.

5. The dilation device of claim 4, wherein a portion of the polymer sleeve which extends beyond the distal end of the metallic shaft defines a polymer distal tip.

6. The dilation device of claim 5, wherein the polymer distal tip defines a distal tip inner diameter sized to contact an outer surface of the guide-wire when installed on the guide-wire for providing a substantially smooth transition from the outer surface of the guide-wire to an outer surface of the dilation device.

7. The dilation device of claim 6, wherein the distal tip inner diameter is less than a metallic shaft inner diameter defined by the metallic shaft.

8. The dilation device of claim 7, further comprising a distal end marker at a distal end region of the dilation device, the distal end marker defining a marker inner diameter substantially equivalent to a distal tip inner diameter defined by the polymer distal tip.

9. The dilation device of claim 7, wherein the distal tip inner diameter is about 0.015 inches and wherein the metallic shaft inner diameter is from between about 0.018 inches to about 0.020 inches.

10. A kit comprising the dilation device of claim 9 and a guide-wire having a diameter of about 0.014 inches.

11. The dilation device of claim 7, wherein the distal tip inner diameter is about 0.036 inches and wherein the metallic shaft inner diameter is from between about 0.038 inches to about 0.040 inches.

12. A kit comprising the dilation device of claim 11 and a guide-wire having a diameter of about 0.035 inches.

13. A kit comprising the dilation device of claim 7 and a guide-wire, wherein a diameter of the guide-wire is between about 93% to about 97% of the distal tip inner diameter, and is between about 80% to about 92% of the metallic shaft inner diameter.

14. The dilation device of claim 5, further comprising a distal end marker at a distal end region of the dilation device, the distal end marker defining a marker inner diameter substantially equivalent to a metallic shaft inner diameter defined by the metallic shaft.

15. The dilation device of claim 1, wherein a metallic shaft inner diameter defined by the metallic shaft is substantially constant along a length of the metallic shaft.

16. The dilation device of claim 15, wherein a metallic shaft outer diameter defined by the metallic shaft is substantially constant along a length of the metallic shaft.

17. The dilation device of claim 16, wherein the metallic shaft comprises a metal tube.

18. The dilation device of claim 17, wherein an outer surface of a distal portion of the metal tube defines a helical-shaped cut to provide flexibility, for facilitating advancement of the dilation device through tortuous vasculature.

19. The dilation device of claim 18, wherein a pitch of the cut decreases distally.

20. A method of traversing a vessel having a lesion therein, the method comprising:
- inserting a guide-wire into the vessel and at least partially through the lesion to create a channel at least partially through the lesion;
- installing a hollow elongated dilation device, having a tapered distal end including a polymer tip with an inner diameter sized for fitting receipt of the guide-wire, along the guide-wire; and
- advancing the dilation device into the lesion so as to dilate a channel containing the guide wire primarily by forcing said lesion radially outwardly from the guide-wire.

21. The method of claim 20, wherein the vessel is a coronary artery.

22. The method of claim 20, wherein the vessel is a peripheral artery.

* * * * *